(12) United States Patent
García Castro et al.

(10) Patent No.: US 10,729,726 B2
(45) Date of Patent: Aug. 4, 2020

(54) IDENTIFICATION AND ISOLATION OF MULTIPOTENT CELLS FROM NON-OSTEOCHONDRAL MESENCHYMAL TISSUE

(71) Applicants: TIGENIX, S.A.U., Madrid (ES); UNIVERSIDAD AUTÓNOMA DE MADRID, Madrid (ES)

(72) Inventors: Rosa Ana García Castro, Madrid (ES); María Gema Fernández Miguel, Madrid (ES); Mariano García Arranz, Madrid (ES); Manuel Angel González De La Peña, Madrid (ES); Damián García Olmo, Madrid (ES)

(73) Assignees: TIGENIX, S.A.U., Madrid (ES); UNIVERSIDAD AUTÓNOMA DE MADRID, Madrid (ES)

(*) Notice: Subject to any disclaimer, the term of this patent is extended or adjusted under 35 U.S.C. 154(b) by 85 days.

(21) Appl. No.: 14/834,006

(22) Filed: Aug. 24, 2015

(65) Prior Publication Data
US 2017/0296585 A1    Oct. 19, 2017

Related U.S. Application Data

(63) Continuation of application No. 11/576,573, filed as application No. PCT/EP2005/010811 on Oct. 4, 2005, now abandoned.

(30) Foreign Application Priority Data

Oct. 4, 2004 (ES) .................................. 200402355

(51) Int. Cl.
| | |
|---|---|
| *G01N 33/53* | (2006.01) |
| *C12N 5/00* | (2006.01) |
| *A61K 35/28* | (2015.01) |
| *C12N 5/074* | (2010.01) |
| *C12N 5/0775* | (2010.01) |
| *C12N 5/0793* | (2010.01) |
| *C12N 5/077* | (2010.01) |
| *G01N 33/50* | (2006.01) |
| *A01N 63/00* | (2020.01) |

(52) U.S. Cl.
CPC ............ *A61K 35/28* (2013.01); *C12N 5/0607* (2013.01); *C12N 5/0619* (2013.01); *C12N 5/0654* (2013.01); *C12N 5/0658* (2013.01); *C12N 5/0667* (2013.01); *G01N 33/5008* (2013.01); *C12N 2506/1384* (2013.01); *C12N 2510/00* (2013.01)

(58) Field of Classification Search
CPC ...... A61K 35/28; C12N 5/0607; C12N 5/667; C12N 5/0658; G01N 33/5008
See application file for complete search history.

(56) References Cited

U.S. PATENT DOCUMENTS

| | | |
|---|---|---|
| 2002/0076400 A1 | 6/2002 | Katz et al. |
| 2003/0082152 A1 | 5/2003 | Hedrick et al. |
| 2005/0019911 A1 | 1/2005 | Gronthos et al. |
| 2005/0153442 A1 | 7/2005 | Katz et al. |
| 2005/0221327 A1* | 10/2005 | Lundgren-Akerlund |
| 2005/0244963 A1 | 11/2005 | Teplyashin |
| 2006/0073124 A1 | 4/2006 | Garcia Castro et al. |
| 2006/0239980 A1* | 10/2006 | Bernad Miana et al. |
| 2007/0248580 A1 | 10/2007 | Garcia Castro et al. |
| 2008/0317718 A1* | 12/2008 | Yoshimura |
| 2009/0292311 A1 | 11/2009 | Garcia Olmo et al. |
| 2010/0172885 A1 | 7/2010 | Pittenger et al. |
| 2012/0027730 A1 | 2/2012 | Delgado et al. |

FOREIGN PATENT DOCUMENTS

| | | |
|---|---|---|
| EP | 1634608 A1 | 3/2006 |
| EP | 1803472 A1 | 7/2007 |
| EP | 2292736 B1 | 1/2015 |
| ES | 2264862 A1 | 1/2007 |
| ES | 2313805 A1 | 3/2009 |
| JP | 2002537849 A | 11/2002 |
| WO | 0053795 A1 | 9/2000 |
| WO | 03022988 A2 | 3/2003 |
| WO | 2005035738 A1 | 4/2005 |
| WO | 2005042730 A2 | 5/2005 |

(Continued)

OTHER PUBLICATIONS

Wallich et al. Gene structure, promoter characterization, and basis for alternative mRNA splicing of the human CD58 gene. J. Immunol. 160:2862-2871, (Year: 1998).*
Jaakkola et al. Human vascular adhesion protein-1 in smooth muscle cells. Am. J. Pathol. 155:1953-1965, (Year: 1999).*
Beresford et al., "Evidence for an Inverse Relationship Between the Differentiation of Adipocytic and Osteogenic Cells in Rat Marrow Stromal Cell Cultures," Journ. of Cell Science, vol. 102, 1992, pp. 341-351.
Caplan, "Mesenchymal Stem Cells," Journal of Orthopedic Research, vol. 9, 1991, pp. 641-650.
Caplan et al., "Mesenchymal Stem Cells: Building Blocks for Molecular Medicine in the 21st Century," Trends in Molecular Medicine, vol. 7, No. 6, Jun. 2001, pp. 259-264.

(Continued)

*Primary Examiner* — Quang Nguyen
(74) *Attorney, Agent, or Firm* — Morrison & Foerster LLP

(57) ABSTRACT

Identification and isolation of multipotent cells from non-osteochondral mesenchymal tissue. This invention relates to the identification and isolation of multipotent cells from non-osteochondral mesenchymal tissue. Specifically, it relates to an adult multipotent cell or a cell population or composition comprising the cell, isolated from non-osteochondral mesenchymal tissue, characterized in that it is positive for the following markers: CD9, CD10, CD13, CD29, CD44, CD49A, CD51, CD54, CD55, CD58, CD59, CD90 and CD105 and because it lacks expression of the following markers: CD11b, CD14, CD15, CD16, CD31, CD34, CD45, CD49f, CD102, CD104, CD106 and CD133.

4 Claims, 28 Drawing Sheets

(56) References Cited

FOREIGN PATENT DOCUMENTS

WO    2006037649 A1    4/2006

OTHER PUBLICATIONS

De Ugarte et al., "Comparison of Multi-Lineage Cells from human Adipose Tissue and Bone Marrow," Cells Tissues Organs, vol. 174, 2003, pp. 101-109.
Friedenstein et al., "Fibroblast Precursors in Normal and Irradiated Mouse Hematopoietic Organs," Exp. Hemat.,, vol. 4, (1976), pp. 267-274.
Haynesworth et al., "Characterization of Cells with Osteogenic Potential from Human Marrow," Bone, vol. 13, (1992), pp. 81-88.
Ivanova et al., "A Stem Cell Molecular Signature," Science, vol. 298, (Oct. 16, 2002), pp. 601-604.
Jiang et al., "Multipotent Progenitor Cells can be Isolated from Postnatal Murine Bone Marrow, Muscle, and Brain," Exp. Hemat., vol. 30, (2002), pp. 896-904.
Morrison et al., "The Biology of Hematopoietic Stem Cells," Annu. Re. Cell Dev. Biol., vol. 11, (1995), pp. 35-71.
Osawa et al., "Long-Term Lymphohematopoietic Reconstitution by a Single CD34-LowlNegative Hematopoietic Stem Cell," Science, vol. 273, (Jul. 12, 1996), pp. 242-245.
Phillips, "Investigating the Genetic Control of Stem Cell Behavior," Curr. Top. Microbiol. Immunol., vol. 251, (2000), pp. 13-19.
Pittenger et al., Multilineage Potential of Adult Human Mesenchymal Stem Cells, Science, vol. 284, No. 5411, (Apr. 2, 1999), pp. 143-147.
Ramalho-Santos et al., -Sternness": Transcriptional Profiling of Embryonic and Adult Stem Cells," Sciece, vol. 298, (Oct. 18, 2002), pp. 597-600.
Rogers et al., "Differentiation Factors Induce Expression of Muscle, Fat, Cartilage, and Bone in a Clone of Mouse Pluripotent Mesenchymal Stem Cells," Am. Surg., vol. 61, No. 3, (Mar. 1995), pp. 231-236.
Sanchez-Ramos et al., "Adult Bone Marrow Stromal Cells Differentiate into Neural Cells in Vitro," Exp. Neurol., vol. 164, No. 2, (2000), pp. 247-256.
Stanford et al., "Rapidly Forming Apatitic Mineral in an Osteoblastic Cell Line (UMR 106-01 BSP)," J. Biol. Chem., vol. 270, No. 16, (Apr. 21, 1995), pp. 9420-9428.
Wakitani et al., "Myogenic Cells Derived from Rat Bone Marrow Mesenchymal Stem Cells Exposed to 5-Azacytidine," Muscle & Nerve, vol. 18, No. 12, (Dec. 1995), pp. 1417-1426.
Yoo et al., "The Role of Osteochondral Progenitor Cells in Fracture Repair," Clin. Orthop., vol. 355, (Oct. 1998), pp. Suppl:S73-S81.
Zuk et al., "Multilineage Cells from Human Adipose Tissue: Implications for Cell-Based Therapies," Tissue Eng., vol. 7, No. 2, (Apr. 2001), pp. 211-228.
Zuk et al., "Human Adipose Tissue is a Source of Multipotent Stem Cells," Molecular Biology of Cell, vol. 13, No. 12, (Dec. 20, 2002), 4279-4295.
Hattori et al., "Osteogenic Potential of Human Adipose Tissue-Derived Stromal Cells as an Alternative Stem Cell Source," Cells Tissues Organs, vol. 178, No. 1, (2004), pp. 2-12.
Lee et al., "Characterization and Expression Analysis of Mesenchymal Stem Cells from Human Bone Marrow and Adipose Tissue," Cellular Physiology and Biochemistry, vol. 14, No. 4-6, (2004), pp. 311-324.
Barry et al., "Mesenchymal Stem Cells: Clinical Applications and Biological Characterization," International Journal of Biochemistry & Cell Biology, vol. 36, No. 4, (Apr. 2004), pp. 568-584.
Cao et al., Human Adipose Tissue-Derived Stem Cells Differentiate into Endothelial Cells in vitro and Improve Postnatal Neovascularization in Vivo, Biochemical and Biophysical Research Communications, vol. 332, No. 2, (Jul. 1, 2005), pp. 370-379.
Asencio Arana et al., "Aproximacion a lost Estudios de los Anastomosis Intestinales Experimentales," Metodos Bioquimicos, Fisicos y Microangiograficos, vol. 46, (1989), pp. 805-810.

Zarapico Romero et al., "La Asociacion Fibrino-Desoxiribonnucleasa en la Profilaxis de la Adherencias Peritoneales Post-Operativas," Rev. Fac. Med., vol. 20, (1972), pp. 347-362.
Shimizu, Kyoko, et al., "Newly developed primary culture of rat visceral adipocytes and their in vitro characteristics.", Cell Biology International 30 (2006) 301-388.
Gonzalez, Manuel A., et al.; "Adipose-Derived Mesenchymal Stem Cells Alleviate Experimental Colitis by Inhibiting Inflammatory and Autoimmune Responses," Gastroenterology, 2009, pp. 978-989, vol. 136.
Gimble, JM, et al.; "Adipose-derived adult stem cells: isolation, characterization, and differentiation potential," Cytotherapy. 2003, pp. 362-369, vol. 5.
Mizuno, Hiroshi; "Versatility of Adipose Tissue as a Source of Stem Cells," J. Nippon Med. Sch., 2003, pp. 428-431, vol. 70.
Rojewski, Markus Thomas, et al.; "Phenotypic Characterization of Mesenchymal Stem Cells from Various Tissues," Transfusion Medicine and Hemotherapy, 2008, pp. 168-184, vol. 35.
Minteer, Danielle, et al.; "Adipose-Derived Mesenchymal Stem Cells: Biology and Potential Applications," Adv. Biochem Eng Biotechnol, 2012, 146.
Aust, L.; "Yield of human adipose-derived adult stem cells from liposuction aspirates," Cytotherapy, 2004, pp. 7-14, vol. 6.
Halme, Dina Gould, et al.; "FDA Regulation of Stem-Cell-Based Therapies," The New England Journal of Medicine, 2006, pp. 1730-1735, vol. 355.
Safwani, Wan Kamarul Zaman Wan, et al.; "The changes of stemness biomarkers expression in human adipose-derived stems cells during long-term manipulation," Biotechnology and Applied Biochemistry, 2011, pp. 261-270, vol. 58.
Torensma, Ruurd, et al.; "The Impact of Cell Source, Culture Methodology, Culture Location and Indicidual Donors on Gene Expression Profiles of Bone Marrow-Derived and Adipose-Derived Stromal Cells," Stem Cells and Development, pp. 1-112, (doi: 10.1089/scd.2012.0384).
McIntosh, Kevin, et al.; "The Immunogenicity of Human Adipose-Derived Cells: Temporal Changes In Vitro," Stem Cells, 2006, pp. 1246-1253, vol. 24.
Garcia-Olmo, Damian, et al.; "Treatment of enterocutaneous fistula in Crohn's Disease with adipose-derived stem cells: a comparison of protocols with and without cell expansion," Int J Colorectal Dis, 2009, pp. 27-30, vol. 24.
Karl, Claudia, et al.; "Neuronal precursor-specific activity of human doublecortin regulatory sequence," Journal of Neurochemistry, 2005, pp. 264-282, vol. 92.
Lee, Youngsoo, et al.; "DNA Ligase IV Suppresses Medulloblastoma Formation," Cancer Research, 2002, pp. 6395-6399, vol. 62.
Young, Michael J., et al.; "Neuronal Differentiation and Morphological Integration of Hippocampal Progenitor Cells Transplanted to the Retina of Immature and Mature Dystrophic Rats," Molecular and Cellular Neuroscience, 2000, pp. 197-205, vol. 16.
Garcia-Olmo, Damian, et al.; "A Phase I Clinical Trial of the Treatment of Crohn's Fistula by Adipose Mesenchymal Stem Cell Transplantation," Diseases of the Colon & Rectum, 2005, pp. 1416-1423, vol. 48.
Zuk, Patricia A., et al.; "Human Adipose Tissue Is a Source of Multipotent Stem Cells," Molecular Biology of the Cell, 2002, pp. 4279-4295, vol. 13.
Horwitz, Edwin M., et al.; "Isolated allogeneic bone marrow-derived mesenchymal cells engraft and stimulate growth in children with osteogenesis imperfecta: Implications for cell therapy of bone," PNAS, 2002, pp. 8932-8937, vol. 99.
Garcí-Olmo, Damian, et al.; "Autologous stem cell transplantation for treatment of rectovaginal fistula in perianal Crohn's disease: a new cell-based therapy," Int J Colorectal Dis, 2003, pp. 451-454, vol. 18.
Gokhale, Ameya, et al.; "Immunosuppression by Co-stimulatory Molecules: Inhibition of CD2-CD48/CD58 Interaction by Peptides from CD2 to Suppress Progression of Collagen-induced Arthritis in Mice," Chem Biol Drug Des, 2013, pp. 106-118, vol. 82.
Mizuno, Hiroshi, et al.; "Mesengenic Potential and Future Clinical Perspective of Human Processed Lipoaspirate Cells," J Nippon Med Sch, 2003, pp. 300-306, vol. 70.

(56) References Cited

OTHER PUBLICATIONS

Zuk, Patricia A., "The Adipose-derived Stem Cell: Looking Back and Looking Ahead," Molecular Biology of the Cell, pp. 1783-1787, vol. 21.

EMA, 2009, "Reflection paper on stem cell-based medicinal products," European Medicines Agency, pp. 1-14.

Alvarez, D.F., et al.; "Publishing flow cytometry data," Am J Physiol Lung Cell Mol Physiol, 2010, pp. L127-L130, vol. 298.

De Ugarte, Daniel A., et al.; "Differential expression of stem cell mobilization-associated molecules on multi-linage cells from adipose tissue and bone marrow," Immunology Letters, 2003, pp. 267-270, vol. 89.

Overton, W. Roy; "Modified Histogram Subtraction Technique for Analysis of Flow Cytometry Data," Cytometry, 1988, pp. 619-626, vol. 9.

Gowda, Shashank, et al.; "Production of Good Manufacturing Practice Grade Equine Adipose-derived Mesenchymal Stem Cells for Therapeutic Use," J. Stem Cell Res. Ther., 2013, pp. 1-11, vol. 3:5.

Gronthos, Stan, et al.; "Surface Protein Characterization of Human Adipose Tissue-Derived Stromal Cells," Journal of Cellular Physiology, 2001, pp. 54-63, vol. 189.

Yoshimura, Kotaro, et al.; "Characterization of Freshly Isolated and Cultured Cells Derived From the Fatty and Fluid Portions of Liposuction Aspirates," Journal of Cellular Physiology, 2006, pp. 64-76, vol. 208.

Le Blanc, Katarina, et al.; Immunobiology of Human Mesenchymal Stem Cells and Future Use in Hematopoietic Stem Cell Transplantation, Biology of Blood and Marrow Transplantation, 2005, pp. 321-334, vol. 11.

Mitchell, James B, et al,; "Immunophenotype of Human Adipose-Derived Cells: Temporal Changes in Stromal-Associated and Stem Cell-Associated Markers," Stem Cells, 2006, pp. 376-385; vol. 24.

\* cited by examiner

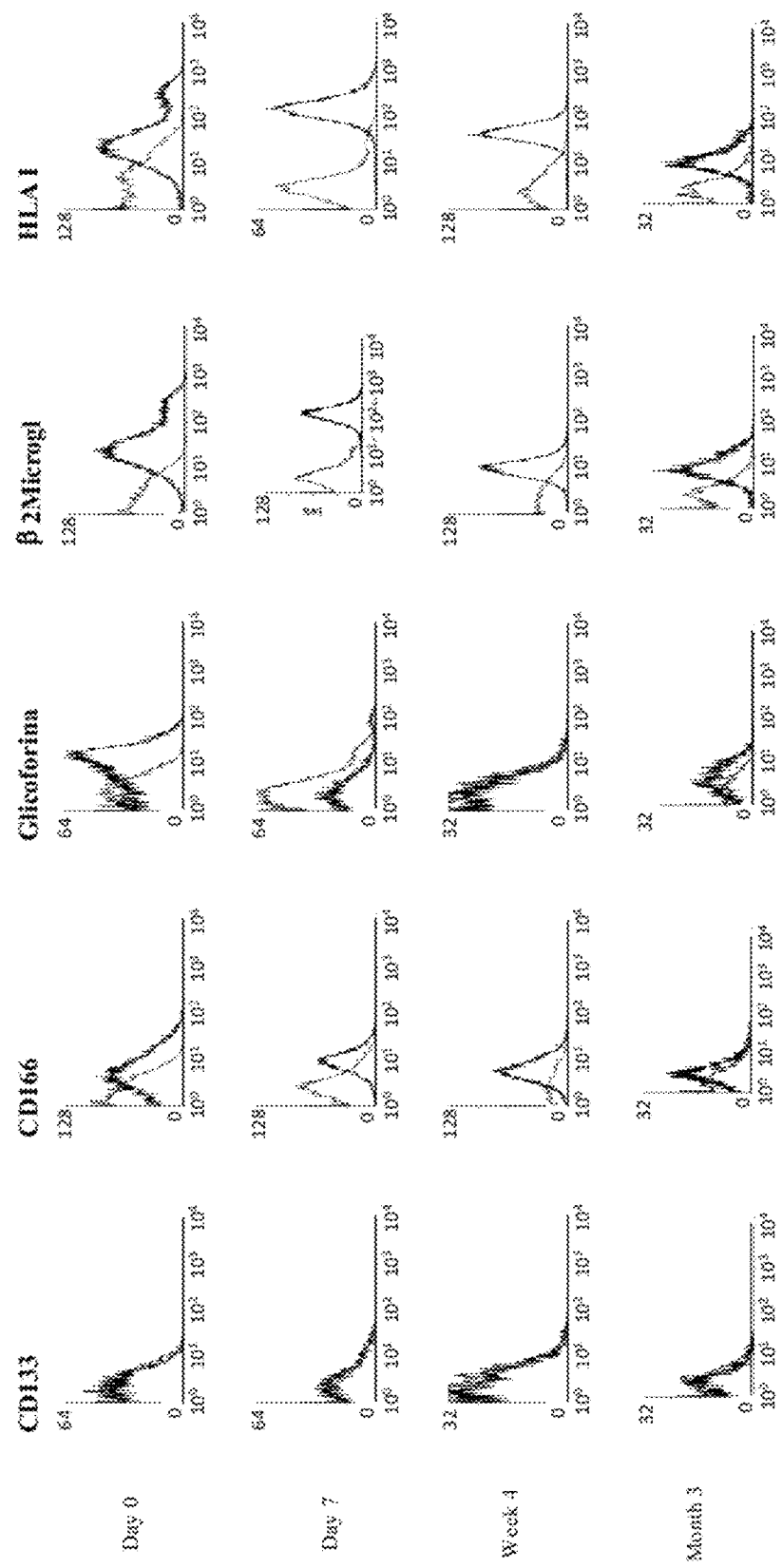

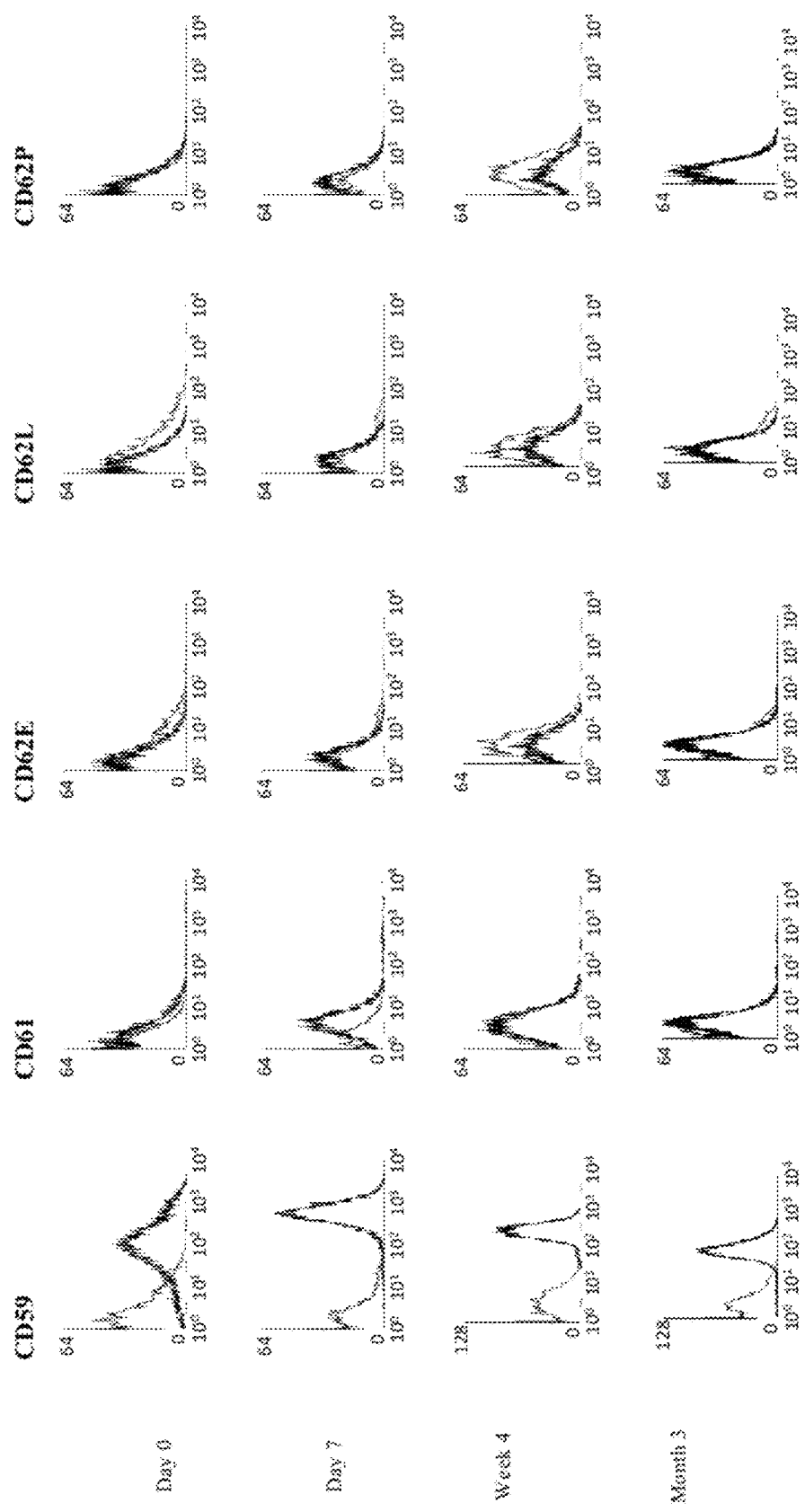

IDENTIFICATION AND ISOLATION OF MULTIPOTENT CELLS FROM NON-OSTEOCHONDRAL MESENCHYMAL TISSUE

CROSS REFERENCE TO RELATED APPLICATIONS

This application is filed under the provisions of 35 U.S.C. § 120 and is a continuation of U.S. patent application Ser. No. 11/576,573 filed on Jul. 13, 2007 entitled "Identification and Isolation of Multipotent Cells from Non-Osteochondral Mesenchymal Tissue" in the name of Rosa Ana GARCIA CASTRO, et al., which is a 35 U.S.C. § 371 filing claiming priority to International Patent Application No. PCT/EP2005/010811, filed on Oct. 4, 2005, which claims priority to Spanish Patent Application No. 200402355, filed on Oct. 4, 2004, all of which are incorporated by reference herein in their entireties.

FIELD OF THE INVENTION

The present invention relates to isolated multipotent adult cells which are isolated from non-osteochondral mesenchymal tissue and are characterized by the presence and absence of a set of cell surface markers. The invention also relates to a method for identifying and isolating a population of said cells, as well as to the applications thereof, for example, in the manufacture of a pharmaceutical composition for the repair and regeneration of tissues.

BACKGROUND OF THE INVENTION

Stem cells show differential characteristics as they are able to sustain themselves and differentiate into one or more cell type. Although research into stem cells and their applications is still in its early stages, adult stem cells in bone marrow have been used in transplants for more than 30 years. Nevertheless, in recent years, stem cell technology has made large advances such that stem cells are currently considered as a promising source of tissue and organs, with an important therapeutic potential for repair and regeneration of tissues.

The use of stem cells is an alternative therapy for several human diseases, particularly those in which there is a loss of functional cells, including chondral, bone and muscular lesions, neurodegenerative diseases, immunologic rejection, heart disease and skin disorders (see U.S. Pat. Nos. 5,811,094, 5,958,767, 6,328,960, 6,379,953, 6,497,875).

In addition to cell therapy applications, stem cells have potential applications in the research and development of new drugs. On the one hand, the study of mechanisms implicated in the proliferation and differentiation of stem cells is of great value in the process of searching for and characterizing new genes involved in a wide range of biological processes, including cell development and differentiation and neoplastic processes (Phillips et al., 2000; Ramalho-Santos et al., 2002; Ivanova et al., 2002). On the other hand, stem cell technology allows specialized cells to be generated and the development of cell models for human and animal diseases, in which the efficacy and toxicity of new active ingredients can be determined in the preclinical phase (U.S. Pat. No. 6,294,346).

An adult somatic stem cell is an undifferentiated cell which is found in differentiated tissue and which has the capacity to proliferate and differentiate into one or more cell types. Adult stem cells are present in different adult tissue, their presence being extensively reported in bone marrow, blood, cornea, retina, brain, muscle, skeleton, dental pulp, gastrointestinal epithelium, liver and skin (Jiang et al., 2002). By their nature, adult stem cells can be used in an autologous setting, and as such, they are immunologically compatibles and their use does not raise any ethical concerns.

An adult stem cell should be able to give rise to fully differentiated cells with mature phenotypes which are integrated into the tissue where they are found and which are able to carry out the specialized functions of the given tissue. The term "phenotype" refers to observable characteristics of the cell, such as characteristic morphology, interactions with other cells and with the extracellular matrix, cell surface proteins (surface markers) and characteristic functions.

Different populations of adult stem cells capable to contribute to the repair of different tissues have been described. Among these populations, those of mesodermic origin are of particular interest because they offer the theoretical possibility of regenerating a large number of clinically very relevant connective tissues such as bone, cartilage, tendons, skeletal muscle, heart muscle, vascular endothelium, subdermal fat and bone marrow stroma. The first cell population of this type isolated was the so-called mesenchymal stem cells (MSC), which are found in bone marrow stroma (Friedenstein et al., 1976; Caplan et al., 1991; Pittenger et al., 1999). These cells have been extensively characterized and studies performed with these cells have shown that they can differentiate into different mesenchymal cell lines such as adipocytes (Beresford et al., 1992), chondrocytes (Johnstone et al., 1998), myoblasts (Wakitani et al., 1995) and osteoblasts (Haynesworth et al., 1992). Likewise, they also have the capacity to differentiate into neurons (Sanchez-Ramos et al., 2000).

The ideal source of adult stem cells is one in which they can be obtained by an easy, non-invasive process and one that allows a sufficient number of cells to be isolated. In particular, a source should provide stem cells that can be easily isolated from a living subject without significant risks and discomfort and the source should allow a high yield to be obtained with minimal contamination from other cell types, without excessive cost of isolation and culture.

The process of obtaining bone marrow is painful and the yield is very low, a substantial increase in the number of cells being necessary by ex vivo expansion, to obtain clinically relevant amount. This step increases cost and makes the procedure time consuming, as well as increases the risk of contamination and loss of material. For these reasons, it would be very desirable to be able to isolate multipotent cells from mesenchymal tissues other than bone marrow. In particular, given their surgical accessibility, it would be convenient to be able to isolate cells from non-osteochondral mesodermal tissues such as, but not limited to, skin, fat and muscle tissue.

The presence of different populations of multipotent adult cells in soft tissues derived from the embryonic mesoderm has been reported by several authors. For example, it has been reported that multipotent cells can be obtained from skeletal muscle and other connective tissue of mammals (Young et al. 1993, Rogers et al. 1995). Multipotent cells have also been obtained from human lipoaspirated tissue (Zuk et al., 2001). Another example of multipotent cells isolated from adult connective tissue is the so-called Multipotent Adult Progenitor Cells (MAPC) obtained from bone marrow (Jiang et al., 2002). In principle, all these isolated cell populations could be used in the repair and regeneration of connective tissue in a similar fashion to the MSC of bone marrow (Caplan et al., 2001). However, except for MAPC, none of these populations has been, until present, sufficiently characterized at the phenotype level. Therefore, although the presence of multipotent adult cells has been described in different connective tissues, in the current state of the art, it is not possible to identify and unequivocally distinguish between different multipotent cell types obtained from soft tissue, or to obtain a substantially pure population.

Currently, phenotype characterization of stem cells comprises determination of markers such as cell surface receptors, among others; and the determination of their capacity for differentiation in vitro cultures. Each cell type has a certain combination of surface markers, that is, it has a certain profile of expression that characterizes that particular cell type, distinguishing it from others.

Different combinations of surface markers have been used for identifying and isolating substantially pure populations of hematopoietic stem cells from the bone marrow of mice, such as: [$Lin^{neg/low}$, $Thy1.1^{low}$, $c-Kit^{high}$, $Sca-1^+$], [$Lin^-$, $Thy1.1^{low}$, $Sca-1^+$, rhodamine $123^{low}$](Morrison, S. J. et al., 1995) or [$Lin^-$, $CD34^{-/int}$, $c-Kit^+$, $Sca-1^+$] (Osawa, M. et al., 1996). Likewise, similar combinations of markers have been used for enriching populations of human hematopoietic stem cells [$Lin^-$, $Thy1^+$, $CD34^+$, $CD38^{neg/low}$](Morrison, S. J. et al., 1995).

Currently, it is not known how many markers associated with compromised and differentiated cells are also present in the different multipotent adult mesenchymal cell populations. For example, a commonly used marker for enriching multipotent adult mesenchymal cells is CD44 (hyaluronic acid receptor). Nevertheless, CD44 is also present in different types of compromised and differentiated cell types. The uncertainty about which markers are associated with the stem cells to allow them to be distinguished from those cells that show a greater degree of differentiation, along with the low percentage of stem cells present in adult cells, has made it difficult to identify and purify populations of multipotent adult mesenchymal cells.

A significant disadvantage in using multipotent adult cells resides in the fact that most of the current sources for obtaining multipotent adult cells are contaminated with other cell types, complicating the process of identification, isolation and characterization of the populations of multipotent adult cells with the objective of using them for therapeutic or other ends. Thus, there is an interest in obtaining a population of multipotent adult cells isolated in a substantially pure form.

The characterization of a multipotent adult cell population from non-osteochondral mesenchymal tissue will allow a method for identification and isolation to be designed, as well as the identification of growth factors associated with self-regeneration. Moreover, there may be growth factors associated with the initial phases of differentiation, knowledge of which would allow more efficient in vivo and ex vivo differentiation, as well as for exercising control over the proliferation of stem cells.

The present invention provides a multipotent adult cell population from non-osteochondral mesenchymal tissue, preferable from adipose tissue, isolated and characterized by means of immunophenotype markers present on the cell surface, showing their multipotent nature.

Similarly, the present invention provides a method for the identification and isolation of a population of multipotent adult cells from non-osteochondral mesenchymal tissue, dependent on a pattern of characteristic immunophenotype markers, allowing a composition of substantially homogeneous multipotent stem cell markers to be obtained.

BRIEF DESCRIPTION OF THE INVENTION

In an aspect, the invention relates to an isolated multipotent adult cell, hereinafter referred to as the multipotent adult cell of the invention, which (a) is isolated from non-osteochondral mesenchymal tissue; (b) expresses CD9<+>, CD10<+>, CD13<+>, CD29<+>, CD44<+>, CD49a<+>, CD51<+>, CD54<+>, CD55<+>, CD58<+>, CD59<+>, CD90<+> and CD105<+>; and (c) lacks expression of CD11b, CD14, CD15, CD16, CD31, CD34, CD45, CD49f, CD102, CD104, CD106 and CD133. The multipotent adult cells of the invention present the capacity to proliferate and to be differentiated into different cell lineages. In a particular embodiment, the multipotent adult cells of the invention can be differentiated into bone phenotype cells, muscle phenotype cells and neuronal phenotype cells.

In another aspect, the invention relates to an isolated cell population that comprises, or consists of, the multipotent adult cells of the invention. In an embodiment, said cell population is nearly, i.e., substantially, homogeneous.

In another aspect, the invention relates to a substantially homogeneous cell composition which comprises a multipotent adult cell of the invention or a cell population of multipotent adult cells of the invention.

In another aspect, the invention relates to a cell that expresses at least one characteristic of a specialized cell, wherein the cell is derived from an isolated multipotent adult cell of the invention. In an embodiment, the invention relates to a cell that expresses at least one characteristic of a specialized cell, wherein the at least one characteristic is that of a cell selected from the group consisting of an epithelial cell, an endothelial cell, an adipocyte, a myocyte, a chondrocyte, an osteocyte, a neuron, an astrocyte, an oligodendrocyte, a hepatocyte, a cardiomyocyte, and a pancreatic cell. An isolated cell population that comprises said cells that express at least one characteristic of a specialized cell, wherein the cells are derived from isolated multipotent adult cells of the invention, constitutes a further aspect of the invention.

In another aspect, the invention relates to a method for obtaining the isolated multipotent adult cells of the invention which comprises:
   a) collecting a non-osteochondral mesenchymal tissue;
   b) obtaining a cell suspension by enzymatic digestion;
   c) sedimentating the cells and resuspending the cells in an appropriate culture medium; and
   d) culturing the cells, and eliminating cells that show no adhesion.

The cells obtained and isolated according to said method contain the characteristics of the multipotent adult cells of the invention, i.e., they (a) have been isolated from non-osteochondral mesenchymal tissue; (b) are positive to the following markers: CD9, CD10, CD13, CD29, CD44, CD49A, CD51, CD54, CD55, CD58, CD59, CD90 and CD105; and (c) lack expression of the following markers: CD11b, CD14, CD15, CD16, CD31, CD34, CD45, CD49f, CD102, CD104, CD106 and CD133. In addition, said cells present the capacity to proliferate and to be differentiated into different cell lineages.

In a preferred embodiment, the non-osteochondral mesenchymal tissue is a connective tissue, preferably adipose tissue. In a still another preferred embodiment, the multipotent adult cells of the invention can be genetically modified.

In another aspect, the invention relates to a method for identifying a population of multipotent adult cells, wherein said population comprises, or consists of, isolated multipotent adult cells of the invention, the method comprising:
   (a) incubating the cells with labelled specific binding compounds for one or more characteristic markers for said population; and
   (b) detecting the presence or absence of binding by the cells to these specific binding compounds.

In a preferred embodiment, said specific binding compound is an antibody.

In another aspect, the present invention relates to a method for isolating a population of multipotent adult cells of the invention, which comprises:
   (a) collecting a non-osteochondral mesenchymal tissue;
   (b) obtaining a cell suspension from the tissue by enzymatic digestion;
   (c) incubating the cell suspension with a labelled compound that binds specifically to one or more of the surface markers characteristic for said population; and
   (d) selecting those cells that have the profile of expression of markers.

The presence or absence of said surface markers characterizes said cells, thus, being characteristic for said cell population. Cells that have the profile of expression of characteristic markers of the multipotent adult cells of the invention are finally selected.

In a preferred embodiment, said method of isolation consists of performing a negative selection, whereby cells that show binding to labelled compounds that bind specifically to a marker selected from the group consisting of CD11b, CD14, CD15, CD16, CD31, CD34, CD45, CD49f, CD102, CD104, CD106 and CD133 are excluded, and a subsequent positive selection, whereby cells that bind to labelled compounds that bind specifically to a marker selected from the group consisting of CD9, CD10, CD13, CD29, CD44, CD49a, CD51, CD54, CD55, CD58, CD59, CD90 and CD105 are selected. Preferably, the labelled compound of specific binding is an antibody.

In another aspect, the invention relates to a multipotent adult cell of the invention, or a population of multipotent adult cells of the invention, for therapeutic use, e.g., for use as a medicament. In an embodiment, the invention relates to a multipotent adult cell of the invention, or to a population of multipotent adult cells of the invention for use in the repair and regeneration of tissues.

Thus, in another aspect, the invention relates to a pharmaceutical composition that comprises a multipotent adult cell of the invention, or a population of multipotent adult cells of the invention, and a pharmaceutically acceptable carrier. In a preferred embodiment, said pharmaceutical composition is useful for the repair and regeneration of tissues.

Further, in another aspect, the invention relates to the use of a multipotent adult cell of the invention, or a cell population of multipotent adult cells of the invention, for the manufacture of a pharmaceutical composition for the repair and regeneration of tissues.

Also, in other aspect, the invention relates to a therapeutic method comprising administering said pharmaceutical composition to a patient in need thereof. In an embodiment, said therapeutic method is for tissue repair or regeneration.

In another aspect, the invention, relates to a method for assessing in vitro or in vivo cell response to a biological or pharmacological agent, or to a combinatorial library of said agents, which comprises:
   (a) isolating a cell population of multipotent adult cells of the invention, wherein the cells are nearly homogeneous,
   (b) expanding the cell population via culturing;
   (c) applying a biological agent or a pharmacological agent or a combinatorial library of said agents to said cell population, and assessing the effects of said agents on the cultured cells.

In an embodiment, the population of multipotent adult cells of the invention of step (a) is isolated from an individual or from a statistically significant population thereof. In other embodiment, the cells of the cell population of multipotent adult cells of the invention of step (a) are nearly, i.e., substantially, homogeneous. In another embodiment, prior to step (c), the cells are allowed to differentiate into a specific type of cells.

BRIEF DESCRIPTION OF THE FIGURES

FIG. 1H shows histograms of fluorescence immunocytometry corresponding to the profile of surface markers CD133, CD166, glycophorin, β2Microg1, and HLA I obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.

FIG. 2F shows histograms of fluorescence immunocytometry corresponding to the profile of surface markers CD59, CD61, CD62E, CD62L, CD62P obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.

DETAILED DESCRIPTION OF THE INVENTION

Figure 1A:
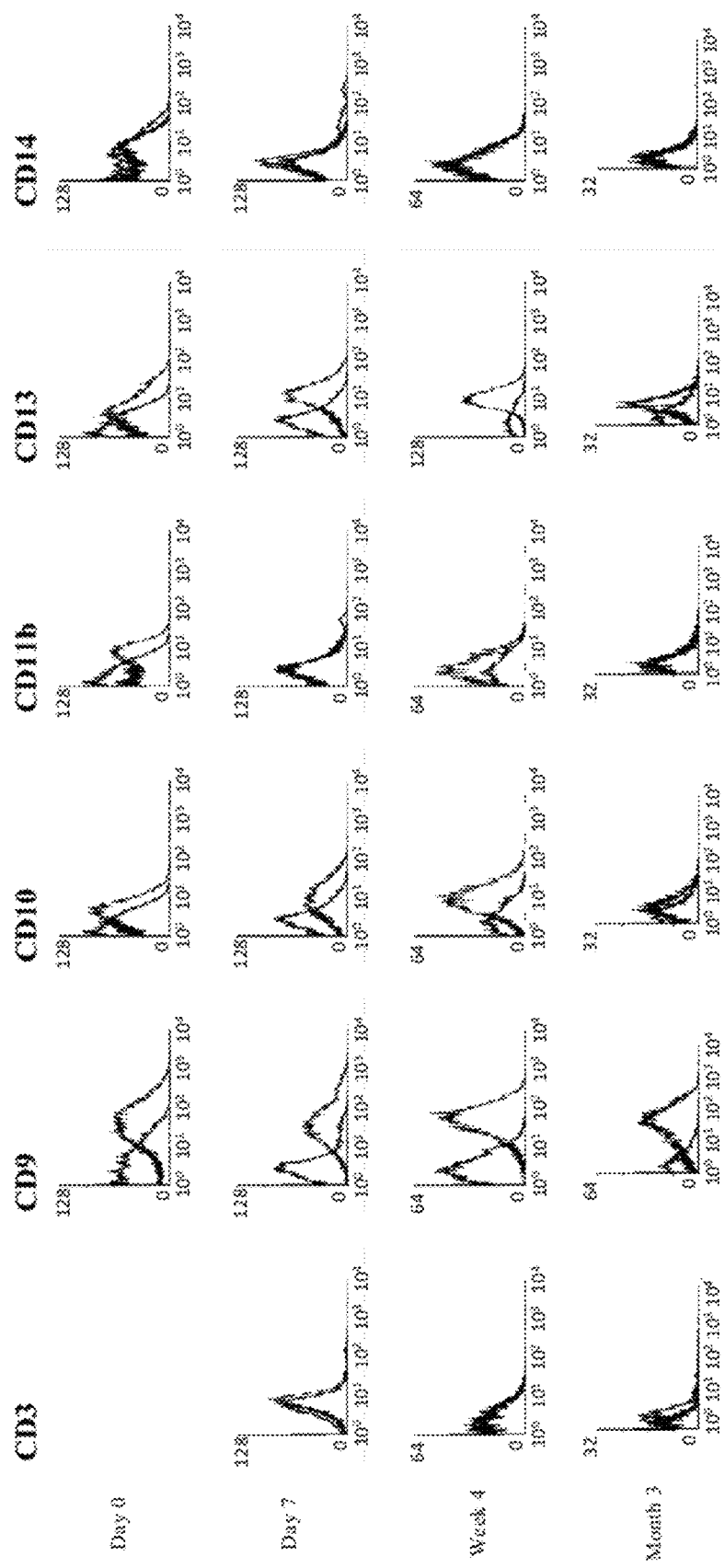
FIG. 1A shows histograms of fluorescence immunocytometry corresponding to the profile of surface markers CD3, CD9, CD10, CD11b, CD13, and CD14 obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.

With the objective of designing an identification and isolation method useful for obtaining a defined population of multipotent adult cells from non-osteochondral mesenchymal tissue ("soft tissue"), the phenotype of recently isolated human mesenchymal cells obtained from sub-dermal adipose tissue was analyzed and also the evolution of surface markers was studied during the expansion of the cells in vitro, as well as their capacity for differentiating into different cell lineages.

Firstly, expression of a series of surface markers on the adult cells from sub-dermal adipose tissue was monitored by flow cytometry when cells were recently isolated and also during the development of the culture in vitro. To do this, a series of commonly used markers were used to identify stem cells, as well as to characterize differentiated cells, including but not limited to: integrins, hematopoietic markers, growth factor receptors and extracellular matrix receptors (Example 1).

The characterization of multipotent adult cells from non-osteochondral mesenchymal tissue by means of determining their immunophenotype profile allows to define said population in terms of the presence or absence of a certain set of surface markers. These markers are epitopes that can be identified using specific antibodies, constituting a valuable tool that allows to identify the population, as well as to design a strategy for isolation or purification thereof.

Subsequently, once characterized, the isolated cells were subjected to differentiation assays with the objective of showing their multipotent nature. To do this, the isolated and characterized cells were induced to in vitro differentiate into cells that express at least one characteristic of a specialized cell. The methods that can be used to induce differentiation of the multipotent adult cells of the present invention into different specific cell types are known by those skilled in the art and some of them are explained in detail in Examples 2, 3 and 4, which show in vitro differentiation of the multipotent adult cells of the invention into bone phenotype cells, muscle phenotype cells and neuronal phenotype cells, respectively.

Therefore, in an aspect, the invention relates to an isolated multipotent adult cell, hereinafter referred to as the multipotent adult cell of the invention, which (a) is isolated from non-osteochondral mesenchymal tissue; (b) expresses CD9<+>, CD10<+>, CD13<+>, CD29<+>, CD44<+>, CD49a<+>, CD51<+>, CD54<+>, CD55<+>, CD58<+>, CD59<+>, CD90<+> and CD105<+>, and (c) lacks expression of CD11b, CD14, CD15, CD16, CD31, CD34, CD45, CD49f, CD102, CD104, CD106 and CD133.

An isolated cell population that comprises, or consists of, the multipotent adult cells of the invention constitutes a further aspect of the present invention. In a particular embodiment, said cell population is nearly, i.e., substantially, homogeneous.

The multipotent adult cells of the invention are isolated from non-osteochondral mesenchymal tissue. The term "non-osteochondral mesenchymal tissue" refers to a mesenchymal tissue other than cartilage and bone marrow. Non-osteochondral mesodermal tissues are also referred in this description to as "soft tissues". Illustrative, non-limitative, examples of non-osteochondral mesodermal tissues include skin, fat and muscle tissue. In a particular embodiment, the multipotent adult cells of the invention are isolated from sub-dermal adipose tissue.

The multipotent adult cells of the invention can be obtained from any suitable source of non-osteochondral mesenchymal tissue from any suitable animal, including human beings. In general, said cells are obtained from non-pathological post-natal mammalian non-osteochondral mesenchymal tissues. In a preferred embodiment, the multipotent adult cells of the invention are obtained from a source of non-osteochondral mesenchymal tissue, such as sub-dermal adipose tissue. Also, in a particular embodiment, the multipotent adult cells of the invention are isolated from a mammal, e.g., a rodent, primate, etc., preferably, from a human being.

The multipotent adult cells of the invention are also characterized by the presence and absence of a set of markers, namely, said cells are characterized in that they (i) are positive for some markers [CD9<+>, CD10<+>, CD13<+>, CD29<+>, CD44<+>, CD49a<+>, CD51<+>, CD54<+>, CD55<+>, CD58<+>, CD59<+>, CD90<+> and CD105<+>], and (ii) are negative for some markers [CD11b, CD14, CD15, CD16, CD31, CD34, CD45, CD49f, CD102, CD104, CD106 and CD133].

The phenotype characterization of the multipotent adult cells of the invention, or of a cell population comprising said cells, by surface markers can be conventionally performed either by individual staining of the cells (flow cytometry) or by making histological cuts of the population in situ, in accordance with conventional methods. In a particular embodiment, the expression of said surface markers on the multipotent adult cells of the invention may be monitored by flow cytometry.

The characterization of the multipotent adult cells of the invention, or a cell population comprising, or consisting of, said cells, by their immunophenotype profile can be used to define said cells or cell population in terms of the presence or absence of a certain set of surface markers. These markers are epitopes that can be identified with specific antibodies, constituting a valuable tool that allows to identify the population, as well as to design a strategy for isolation or purification thereof. Monoclonal antibodies against said surface markers can be used to identify the multipotent adult cells of the invention.

The determination of the profile of surface markers by antibodies (immunophenotype characterization) may be direct, using a labelled antibody, or indirect, using a second labelled antibody against the primary specific antibody of the cell marker, thus achieving signal amplification.

On the other hand, the presence or absence of binding of the antibody may be determined by different methods that include but are not limited to immunofluorescence microscopy and radiography. Similarly, it is possible to carry out the monitoring of the levels of binding of the antibody by flow cytometry, a technique that allows the levels of fluorochrome to be correlated with the quantity of antigens present on the cell surface bound specifically to the labelled antibodies.

In the assay of identification and isolation, the cell population comes into contact with a specific reagent, labelled or not, depending on whether the assay is performed by a direct or indirect detection method, respectively. The term "specific reagent" refers to a member of a specific binding pair; members of a specific binding pair, include but are not limited to, binding pairs of antigens and antibodies, pairs comprising MHC antigens and T-cell receptors, complementary nucleotide sequences, as well as pairs of peptide ligands and their receptor. The specific binding pairs include analogues, fragments and derivatives of the specific member of the binding pair.

The use of antibodies as reagents with affinity is of particular interest. The production of specific monoclonal antibodies will be evident to any ordinary skilled person in the art. In experiments of identification or separation of cell populations, the antibodies are labelled. For this purpose, markers that are used include but are not limited to: magnetic particles, biotin and fluorochromes that will allow identification or separation of the cell type to which the antibody has bound. Thus, for example, the analysis of the cell population comprising the multipotent adult cells of the invention by flow cytometry allows different antibodies labelled with fluorochromes that emit at different wavelengths to be used in the same sample. Thus, it is possible to know the specific profile of the population for these surface markers, as well as carry out a separation for the set of markers used.

The separation of the populations that present the phenotype of interest can be carried out by affinity separation techniques, which include magnetic separation (using magnetic particles coated with specific antibodies), affinity chromatography, cytotoxic agents bound to monoclonal antibodies or used along with monoclonal antibodies and panning with the antibody attached to a solid support, as well as by other techniques that are appropriate. A more precise separation would be obtained by flow cytometry, a technique that allows the separation of cell populations according to the intensity of staining, along with other parameters such as cell size and cell complexity.

The multipotent adult cells of the invention present the capacity to proliferate and to be differentiated into different cell lineages. Illustrative, non-limitative examples of cell lineages in which the multipotent adult cells of the invention can be differentiated include, e.g., bone phenotype cells, muscle phenotype cells and neuronal phenotype cells.

The multipotent adult cells of the invention can proliferate and differentiate into cells of other lineages by conventional methods. Methods of identifying and subsequently isolating differentiated cells from their undifferentiated counterparts can be also carried out by methods well known in the art.

The multipotent adult cells of the invention are also capable of being expanded ex vivo. That is, after isolation, the multipotent adult cells of the invention can be maintained and allowed to proliferate ex vivo in culture medium. Such medium comprises, for example, Dulbecco's Modified Eagle's Medium (DMEM), antibiotics, and glutamine, and it is usually supplemented with 2-20% fetal bovine serum (FBS). It is within the skill of one in the art to modify or modulate concentrations of media and/or media supplements as necessary for the cells used. Sera often contain cellular factors and components that are necessary for viability and expansion. Examples of sera include FBS, bovine serum (BS), calf serum (CS), fetal calf serum (FCS), newborn calf serum (NCS), goat serum (GS), horse serum (HS), porcine serum, sheep serum, rabbit serum, rat serum (RS), etc. Also it is contemplated, if the multipotent adult cells of the invention are of human origin, supplementation of cell culture medium with a human serum, preferably of autologous origin. It is understood that sera can be heat-inactivated at 55-65° C. if deemed necessary to inactivate components of the complement cascade. Modulation of serum concentrations, withdrawal of serum from the culture medium can also be used to promote survival of one or more desired cell types. Preferably, multipotent adult cells of the invention will benefit from FBS concentrations of about 2% to about 25%. In another embodiment, the multipotent adult cells of the invention can be expanded in a culture medium of definite composition, in which the serum is replaced by a combination of serum albumin, serum transferrin, selenium, and recombinant proteins including but not limited to: insulin, platelet-derived growth factor (PDGF), and basic fibroblast growth factor (bFGF).

Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, and the like.

Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromacin, kanamycin, mitomycin, etc.

Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

The maintenance conditions of the multipotent adult cells of the invention can also contain cellular factors that allow cells to remain in an undifferentiated form. It is apparent to those skilled in the art that prior to differentiation supplements that inhibit cell differentiation must be removed from the culture medium. It is also apparent that not all cells will require these factors. In fact, these factors may elicit unwanted effects, depending on the cell type.

The multipotent adult cells of the invention can be transfected or genetically engineered to express, at least, one polypeptide of interest. In an embodiment, the polypeptide of interest is a product capable of inducing or increasing the expression of genes involved in the repair or regeneration of a tissue.

In another aspect, the invention relates to a method for obtaining the isolated multipotent adult cells of the invention which comprises:
 a) collecting a non-osteochondral mesenchymal tissue;
 b) obtaining a cell suspension by enzymatic digestion;
 c) sedimentating the cells and resuspending the cells in an appropriate culture medium; and
 d) culturing the cells in a solid surface, and eliminating cells that show no adhesion to said solid surface.

The cells obtained according to said method contain the characteristics of the multipotent adult cells of the invention.

As used herein, the term "solid surface" refers to any material that allow the multipotent adult cells of the invention to adhere. In a particular embodiment said material is a plastic material treated to promote the adhesion of mammalian cells to its surface.

Steps a)-d) can be carried out by conventional techniques known by those skilled in the art. Briefly, the multipotent adult cells of the invention can be obtained by conventional means from any suitable source of non-osteochondral mesenchymal tissue from any suitable animal, including human beings, e.g., from human adipose tissue. The animal can be alive or dead, so long as non-osteochondral mesenchymal tissue cells within the animal are viable. Typically, human adipose cells are obtained from living donors, using well-recognized protocols such as surgical or suction lipectomy. Indeed, as liposuction procedures are so common, liposuction effluent is a particularly preferred source from which the cells of the invention can be derived. Thus, in a particular embodiment, the multipotent adult cells of the invention are from human sub-dermal adipose tissue obtained by liposuction.

The sample of non-osteochondral mesenchymal tissue is, preferably, washed before being processed. In a protocol, the sample of non-osteochondral mesenchymal tissue is washed with physiologically-compatible saline solution (e.g., phosphate buffered saline (PBS)) and then vigorously agitated and left to settle, a step that removes loose matter (e.g., damaged tissue, blood, erythrocytes, etc) from the tissue. Thus, the washing and settling steps generally are repeated until the supernatant is relatively clear of debris. The remaining cells generally will be present in lumps of various sizes, and the protocol proceeds using steps gauged to degrade the gross structure while minimizing damage to the cells themselves. One method of achieving this end is to treat the washed lumps of cells with an enzyme that weakens or destroys bonds between cells (e.g., collagenase, dispase, trypsin, etc.). The amount and duration of such enzymatic treatment will vary, depending on the conditions employed, but the use of such enzymes is generally known in the art. Alternatively or in conjunction with such enzymatic treatment, the lumps of cells can be degraded using other treatments, such as mechanical agitation, sonic energy, thermal energy, etc. If degradation is accomplished by enzymatic methods, it is desirable to neutralize the enzyme following a suitable period, to minimize deleterious effects on the cells.

The degradation step typically produces a slurry or suspension of aggregated cells and a fluid fraction containing generally free stromal cells (e.g., red blood cells, smooth muscle cells, endothelial cells, fibroblast cells, and stem cells). The next stage in the separation process is to separate the aggregated cells from the cells of the invention. This can be accomplished by centrifugation, which forces the cells into a pellet covered by a supernatant. The supernatant then can be discarded and the pellet suspended in a physiologically-compatible fluid. Moreover, the suspended cells typically include erythrocytes, and in most protocols it is desirable to lyse them. Methods for selectively lysing erythrocytes are known in the art, and any suitable protocol can be employed (e.g., incubation in a hyper- or hypotonic medium, by lysis using ammonium chloride, etc.). Of course, if the erythrocytes are lysed, the remaining cells should then be separated from the lysate, for example by filtration, sedimentation, or density fractionation.

Regardless of whether the erythrocytes are lysed, the suspended cells can be washed, re-centrifuged, and resuspended one or more successive times to achieve greater purity. Alternatively, the cells can be separated on the basis of cells surface markers profile or on the basis of cell size and granularity.

Following the final isolation and resuspension, the cells can be cultured and, if desired, assayed for number and viability to assess the yield. Desirably, the cells will be cultured without differentiation, on a solid surface, using a suitable cell culture media, at the appropriate cell densities and culture conditions. Thus, in a particular embodiment, cells are cultured without differentiation on a solid surface, usually made of a plastic material, such as Petri dishes or cell culture flasks, in the presence of a suitable cell culture medium [e.g., DMEM, typically supplemented with 5-15% (e.g., 10%) of a suitable serum, such as fetal bovine serum or human serum], and incubated under conditions which allow cells to adhere to the solid surface and proliferate. After incubation, cells are washed in order to remove non-adhered cells and cell fragments. The cells are maintained in culture in the same medium and under the same conditions until they reach the adequate confluence, typically, about 80% cell confluence, with replacement of the cell culture medium when necessary. After reaching the desired cell confluence, the cells can be expanded by means of consecutive passages using a detachment agent such as trypsin and seeding onto a bigger cell culture surface at the appropriate cell density (usually 2,000-10,000 cells/cm$^2$). The cells can be passaged some times without losing their developmental phenotype. Typically, the cells are plated at a desired density such as between about 100 cells/cm$^2$ to about 100,000 cells/cm$^2$ (such as about 500 cells/cm$^2$ to about 50,000 cells/cm$^2$, or, more particularly, between about 1,000 cells/cm$^2$ to about 20,000 cells/cm$^2$). If plated at lower densities (e.g., about 300 cells/cm$^2$), the cells can be more easily clonally isolated. For example, after a few days, cells plated at such densities will proliferate into an homogeneous population. In a particular embodiment, the cell density is between 2,000-10,000 cells/cm$^2$.

Cells which remain adhered to the solid surface are selected and the phenotype thereof is analyzed by conventional methods in order to confirm the identity of the multipotent adult cells of the invention as will be mentioned below. Cells which remain finally adhered to the solid surface constitute a homogeneous cell population of multipotent adult cells of the invention. Example 1 describes in a detailed manner the isolation of multipotent adult cells of the invention from human sub-dermal adipose tissue.

Usually, cells which remain adhered to the solid surface show the desired phenotype, although it has to be confirmed so that the cells can be used according to the invention. Therefore, the adhesion of cells to the solid surface constitutes a criteria for selecting the multipotent adult cells of the invention. Confirmation of the phenotype of interest can be carried out by using conventional means.

Cell-surface markers can be identified by any suitable conventional technique, usually based on a positive/negative selection; for example, monoclonal antibodies against cell-surface markers, which presence/absence in the cells has to be confirmed, can be used; although other techniques can also be used. Thus, in a particular embodiment, monoclonal antibodies against CD9, CD10, CD13, CD29, CD44, CD49a, CD51, CD54, CD55, CD58, CD59, CD90 and CD105 are used in order to confirm the absence of said markers in the selected cells; and monoclonal antibodies against CD11b, CD14, CD15, CD16, CD31, CD34, CD45, CD49f, CD102, CD104, CD106 and CD133 are used in order to confirm the absence of said markers in the selected cells. Said monoclonal antibodies are known or can be obtained by a skilled person in the art by conventional methods.

The capacity of the selected cells to differentiate into different cell lineages can be assayed by conventional methods as previously disclosed.

The multipotent adult cells of the invention and cell populations provided by the instant invention can be clonally expanded, if desired, using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). Of course, the cells can be cloned by plating them at low density (e.g., in a Petri dish or other suitable substrate) and isolating them from other cells using devices such as a cloning rings.

The production of a clonal population can be expanded in any suitable culture medium. In any event, the isolated cells can be cultured to a suitable point when their developmental phenotype can be assessed.

Further assays carried out by the inventors have shown that ex vivo expansion of the cells of the invention without inducing differentiation can be accomplished for extended time periods by using specially screened lots of suitable serum (such as fetal bovine serum or human serum). Methods for measuring viability and yield are known in the art (e.g., trypan blue exclusion).

Any of the steps and procedures for isolating the cells of the cell population of the invention can be performed manually, if desired. Alternatively, the process for isolating such cells can be facilitated through a suitable device, many of which are known in the art.

In another aspect, the invention relates to a method for identifying a population of multipotent adult cells, wherein said population comprises, or consists of, multipotent adult cells of the invention, the method comprising:

(a) incubating the cells with labelled specific binding compounds for one or more characteristic markers for said population; and (b) detecting the presence or absence of binding by the cells to these specific binding compounds.

This method can be carried out as previously mentioned in connection with the immunophenotype characterization of the cells of the invention. In a preferred embodiment, said specific binding compound is an antibody.

In another aspect, the present invention relates to a method for isolating a population of multipotent adult cells of the invention, which comprises:

(a) collecting a non-osteochondral mesenchymal tissue;
(b) obtaining a cell suspension from the tissue by enzymatic digestion;
(c) incubating the cell suspension with a labelled compound that binds specifically to one or more of the surface markers characteristic for said population; and
(d) selecting those cells that have the profile of expression of markers.

The presence or absence of said surface markers characterizes said cells, thus, being characteristic for said cell population. Cells that have the profile of expression of characteristic markers of the multipotent adult cells of the invention are finally selected.

In a preferred embodiment, said method of isolation consists of performing a negative selection, whereby cells are excluded that show binding to labelled compounds that bind specifically to a marker selected from the group consisting of CD11b, CD14, CD15, CD16, CD31, CD34, CD45, CD49f, CD102, CD104, CD106 and CD133, and a subsequent positive selection, whereby cells are selected that bind to labelled compounds that bind specifically to a marker selected from the group consisting of CD9, CD10, CD13, CD29, CD44, CD49a, CD51, CD54, CD55, CD58, CD59, CD90 and CD105. Preferably, the labelled compound of specific binding is an antibody.

This method can be carried out as previously mentioned in connection with the method for obtaining the multipotent adult cells of the invention.

The multipotent adult cells of the invention, or a cell population of multipotent adult cells of the invention, can be found in a cell composition. Therefore, in another aspect, the invention relates to a substantially homogeneous cell composition which comprises a multipotent adult cell of the invention or a cell population of multipotent adult cells of the invention.

The multipotent adult cells of the invention can be used for repairing and regenerating tissues. Thus, in another aspect, the invention relates to a multipotent adult cell of the invention, or a population of multipotent adult cells of the invention, for therapeutic use, e.g., for use as a medicament. In an embodiment, the invention relates to a multipotent adult cell of the invention, or to a population of multipotent adult cells of the invention for use in the repair and regeneration of tissues.

In another aspect, the invention relates to a pharmaceutical composition that comprises a multipotent adult cell of the invention, or a population of multipotent adult cells of the invention, and a pharmaceutically acceptable carrier. In a preferred embodiment, said pharmaceutical composition is useful for the repair and regeneration of tissues.

Combinations of two or more of type of multipotent adult cells of the invention are included within the scope of the pharmaceutical compositions provided by the instant invention.

The pharmaceutical composition of the invention comprises a prophylactically or therapeutically effective amount of a multipotent adult cell of the invention, or a cell population of multipotent adult cells of the invention, and a pharmaceutically acceptable carrier. In a specific embodiment, the term "pharmaceutically acceptable" means approved by a regulatory agency of the Federal or a state government or listed in the U.S. Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E. W. Martin. Such compositions will contain a prophylactically or therapeutically effective amount of a multipotent adult cell of the invention, or a cell population of multipotent adult cells of the invention preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

The administration of the cells or cell population of the invention, or the pharmaceutical composition comprising same, to the subject in need thereof can be carried out by conventional means. In a particular embodiment, said cells or cell population is administered to the subject by a method which involves transferring the cells to the desired tissue, either in vitro or in vivo, to the animal tissue directly. The cells can be transferred to the desired tissue by any appropriate method, which generally will vary according to the tissue type. For example, cells can be seeded onto the desired site within the tissue to establish a population, etc. Cells can be transferred to sites in vivo using devices such as catherters, trocars, cannulae, stents (which can be seeded with the cells), etc.

The pharmaceutical composition of the invention can be used in a combination therapy. In a specific embodiment, the combination therapy is administered to a subject in need of treatment, such as a patient in need of repair or regeneration of a tissue. In an embodiment, the combination therapy is used in conjunction with other types of treatments to repair or regenerate tissues. In accordance with the above embodiment, the combination therapies of the invention can be used prior to, concurrently or subsequent to the administration of the multipotent adult cells of the invention.

Also, in another aspect, the invention relates to the use of a multipotent adult cell of the invention, or a cell population of multipotent adult cells of the invention, for the manufacture of a pharmaceutical composition for the repair and regeneration of tissues.

The invention further relates, in another aspect, to a therapeutic method comprising administering said pharmaceutical composition to a patient in need thereof. In an embodiment, said therapeutic method is for tissue repair or regeneration.

In another aspect, the invention, relates to a method for assessing in vitro or in vivo cell response to a biological or pharmacological agent, or to a combinatorial library of said agents, which comprises:
  (a) isolating a cell population of multipotent adult cells of the invention, wherein the cells are nearly homogeneous,
  (b) expanding the cell population via culturing;
  (c) applying a biological agent or a pharmacological agent or a combinatorial library of said agents to said cell population, and assessing the effects of said agents on the cultured cells.

In an embodiment, the population of multipotent adult cells of the invention of step (a) is isolated from an individual or from a statistically significant population thereof. In other embodiment, the cells of the cell population of multipotent adult cells of the invention of step (a) are nearly, i.e., substantially, homogeneous. In another embodiment, prior to step (c), the cells are allowed to differentiate into a specific type of cells.

Further, in another aspect, the invention relates to a cell that expresses at least one characteristic of a specialized cell, wherein the cell is derived from an isolated multipotent adult cell of the invention. These cells are also multipotent adult cells having a differentiation stage more advanced than that of the multipotent adult cells of the invention. In an embodiment, the invention relates to a cell that expresses at least one characteristic of a specialized cell, wherein the at least one characteristic is that of a cell selected from the group consisting of an epithelial cell, an endothelial cell, an adipocyte, a myocyte, a chondrocyte, an osteocyte, a neuron, an astrocyte, an oligodendrocyte, a hepatocyte, a cardiomyocyte, and a pancreatic cell. An isolated cell population that comprises said cells that express at least one characteristic of a specialized cell, wherein the cells are derived from the isolated multipotent adult cells of the invention, constitutes a further aspect of the invention.

The following examples are presented to illustrate the invention, but they in no way limit it.

Example 1

Isolation of Multipotent Adult Cells from Soft Tissue and Characterization of Surface Markers The isolation of multipotent adult cells from soft tissue was performed by selecting those cells with a capacity for proliferation and differentiation, characterized in that they show adhesion to the plastic container of the cell culture. Then, the cells were characterized by monitoring by flow cytometry the expression of a series of surface markers on the recently isolated cells and during the course of the culture development in vitro.

The isolation of the multipotent adult cells was carried out from sub-dermal adipose tissue, obtained by liposuction from 3 healthy human donors (donors 1, 2 and 3). First, the sample from the sub-dermal adipose tissue was washed with phosphate buffered saline solution (PBS). To achieve destruction of the extracellular matrix and the isolation of the cells, an enzymatic digestion was performed with type II collagenase in saline solution (5 mg/ml) at 37° C. for 30 minutes. The collagenase was deactivated by adding an equivalent volume of DMEM medium, with 10% fetal bovine serum. This cell suspension was centrifuged at 250 g for 10 minutes to obtain a cell deposit.

$NH_4Cl$ was added at an end concentration of 0.16 M and the mixture was incubated for 10 minutes at room temperature to induce the lysis of the erythrocytes present. The suspension was centrifuged at 250-400 g and resuspended in DMEM-10% FBS with 1% ampicillin-streptomycin. Finally, the cells were plated, inoculating $2 \times 10^4$-$3 \times 10^4$ cells per $cm^2$.

The cells were cultured for 20-24 hours at 37° C., under an atmosphere with 5% $CO_2$. After 24 hours, the culture was washed with PBS to remove the cells and the remains of the tissue in suspension. The cells selected by adhesion to the plastic container were cultured in DMEM+10% fetal bovine serum (FBS).

After isolation, the multipotent adult cells isolated were characterized from one of the donors, in function of the presence/absence of a series of surface markers. To do this, the expression of the following surface markers was monitored by flow cytometry:

Intedrin: CD11 b, CD18, CD29, CD49a, CD49b, CD49c, CD49d, CD49e, CD49f, CD51, CD61, CD104.
Hematopoietic markers: CD3, CD9, CD10, CD13, CD14, CD16, CD19, CD28, CD34, CD38, CD45, CD90, CD133 and glycophorin.
Growth factor receptors: CD105, NGFR.
Extracellular matrix receptors: CD15, CD31, CD44, CD50, CD54, CD62E, CD62L, CD62P, CD102, CD106, CD166.
Others: CD36, CD55, CD56, CD58, CD59, CD95, HLA-I, HLA-II, β2-microglobuline.

The immunophenotype characterization of the cells was performed on recently isolated cells and also on day 7, after 4 weeks and after 3 months of culture, of the samples from the 3 healthy human donors. Taking into account that the selection is performed by adhesion to the plastic container of the cell culture, cells from the cell fraction adhered after less than 24 hours in the culture since isolation are considered as "recently isolated cells".

The cells to be characterized were collected by means of gentle digestion with trypsin, washed with PBS and incubated for 30 minutes at 4° C. with fluorescein (FITC) or phycoerythrin (PE) labelled antibodies against each one of the cell surface markers to be analyzed. The cell markers were washed and immediately analyzed using the Epics-XL cytometer (Coulter). As controls, cells stained with unspecific, FITC or PE labelled, antibodies of the corresponding isotypes were used.

Figure 1B:
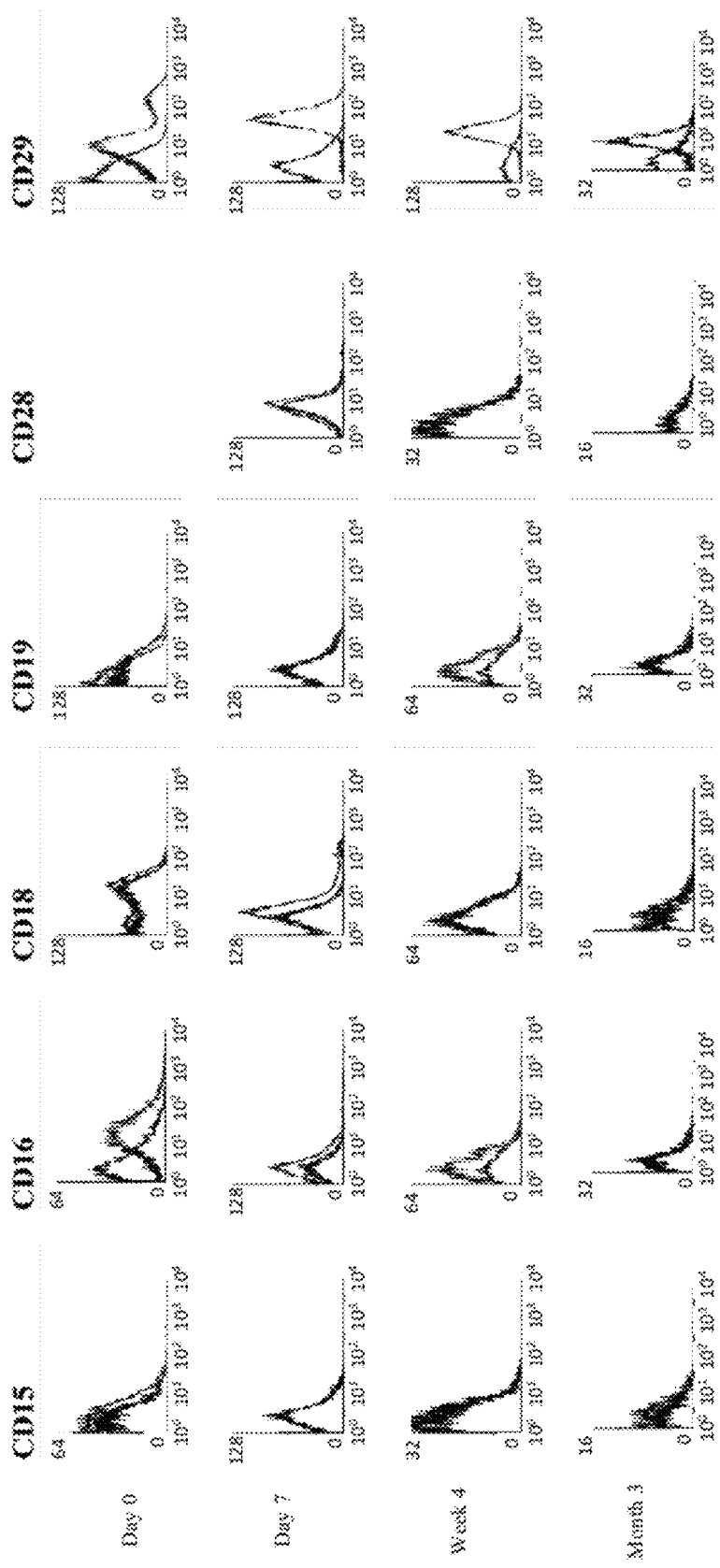
FIG. 1B shows histograms of fluorescence immunocytometry corresponding to the profile of surface markers CD15, CD16, CD18, CD19, CD28, and CD 29 obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1C:
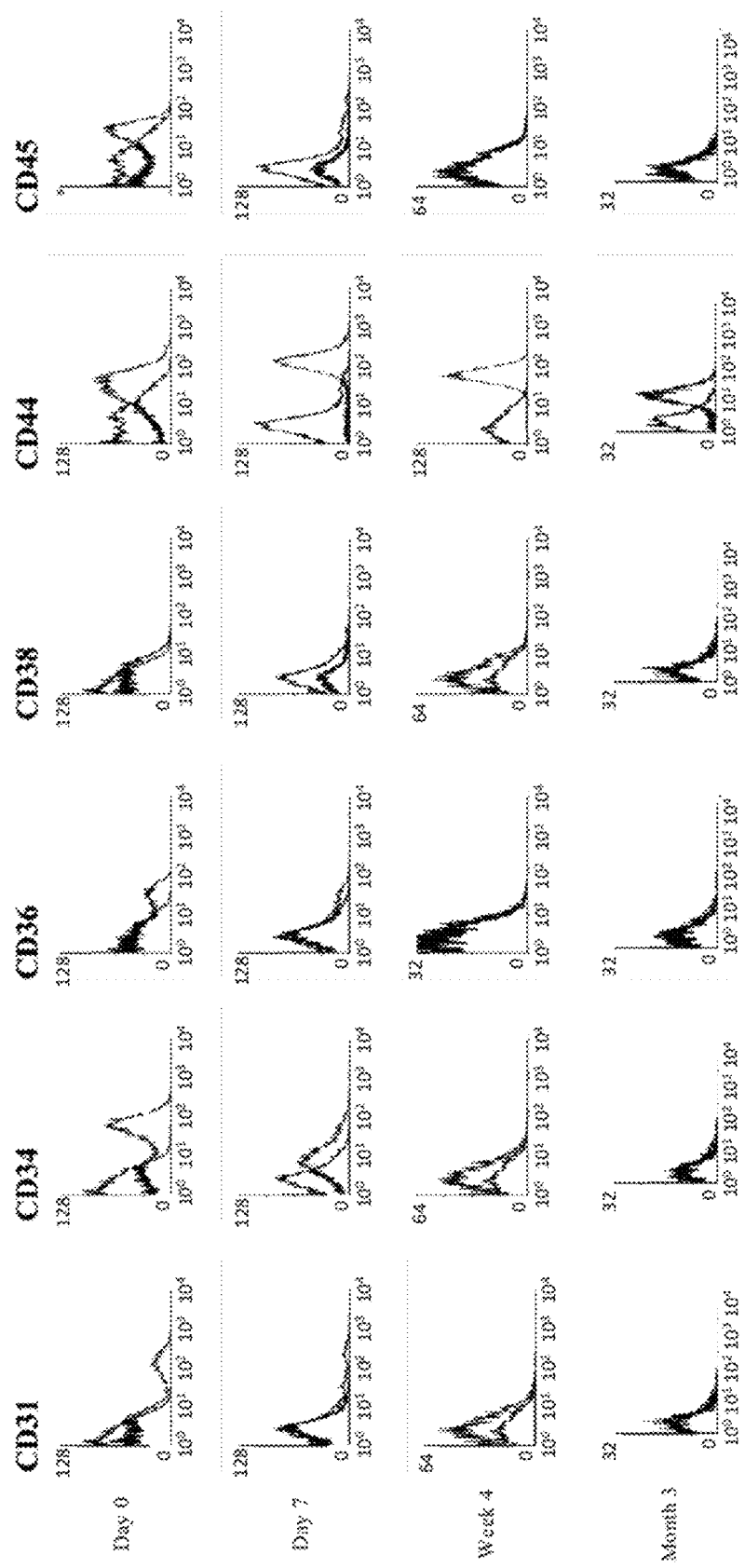
FIG. 1C shows histograms of fluorescence immunocytometry corresponding to the profile of surface markers CD31, CD34, CD36, CD38, CD44, and CD45 obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1D:
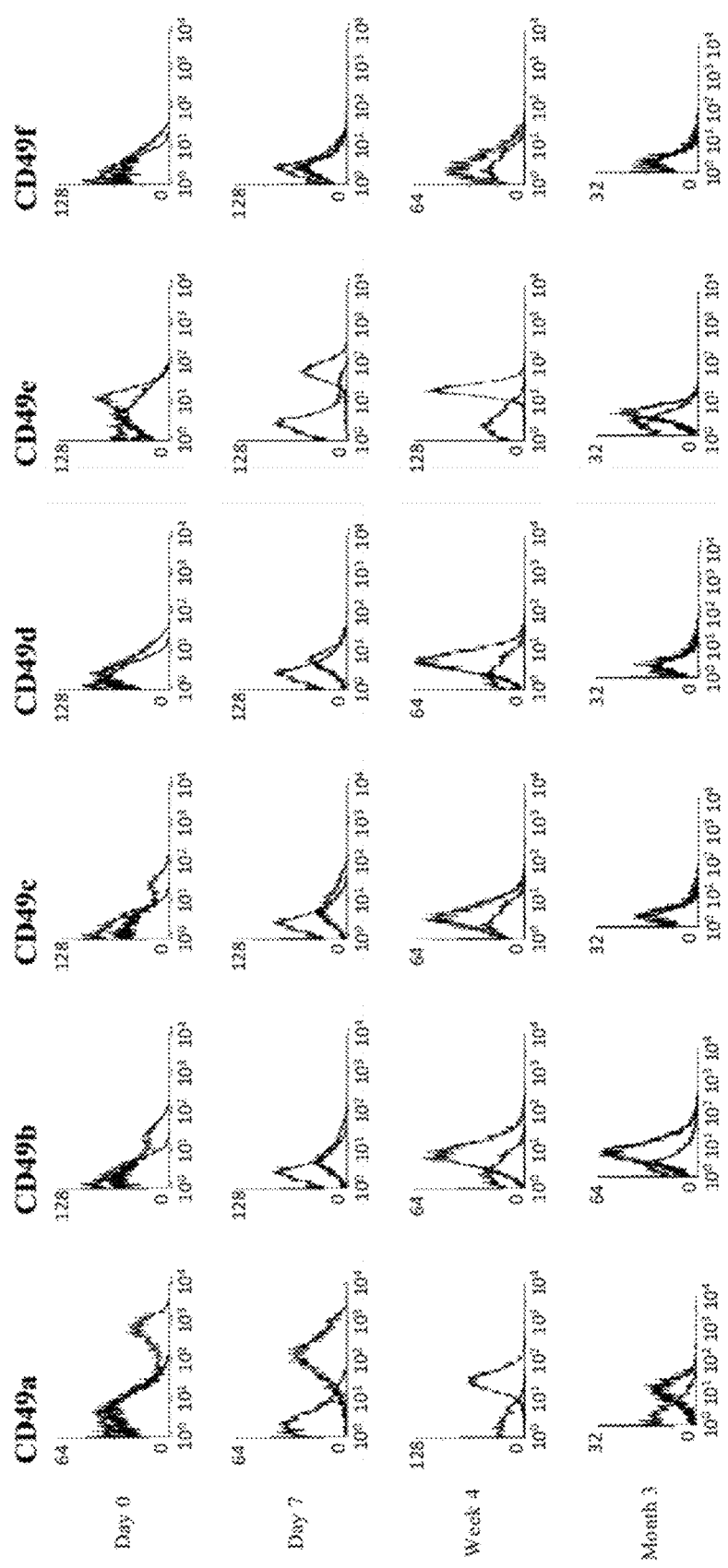
FIG. 1D shows histograms of fluorescence immunocytometry corresponding to the profile of surface markers CD49a, CD49b, CD49c, CD49d, CD49e, and CD49f obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1E:
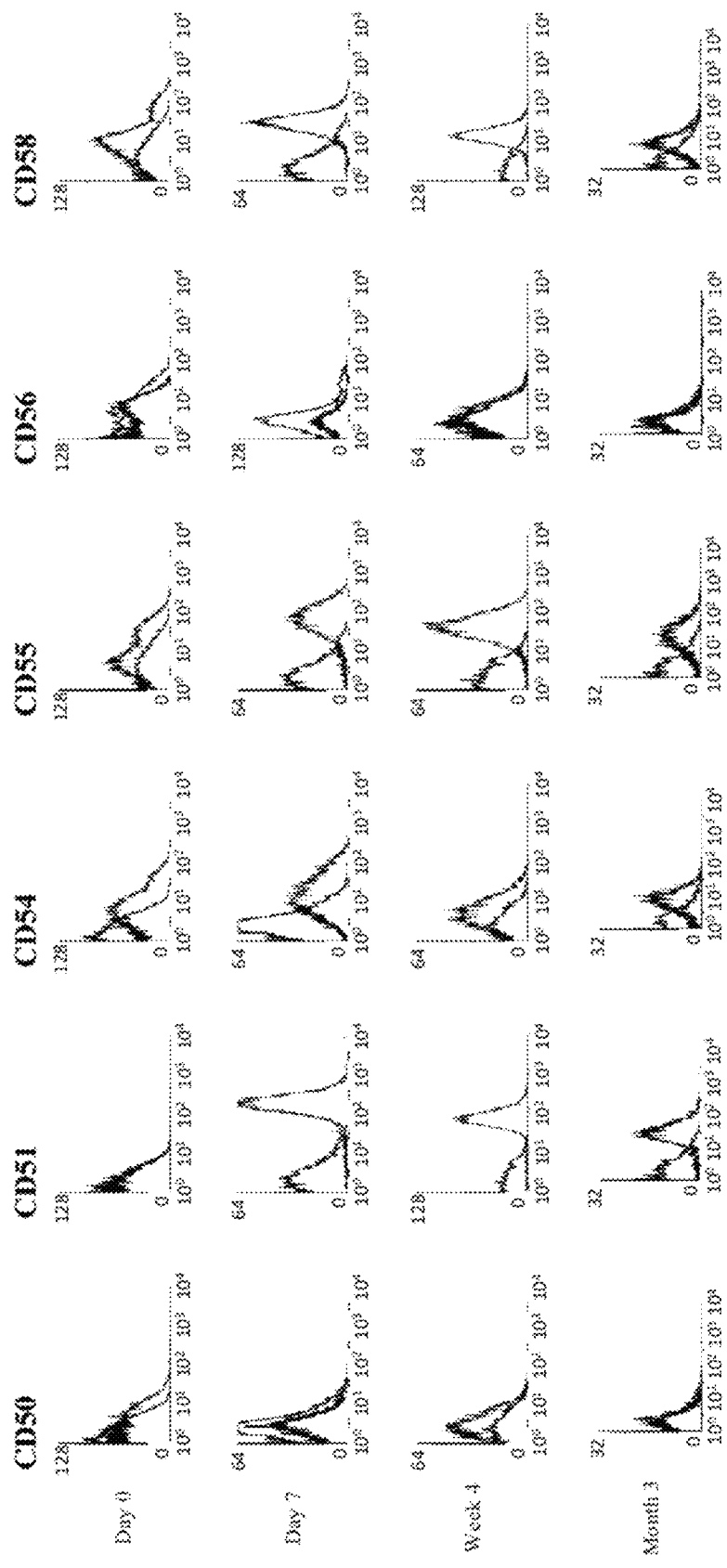
FIG. 1E shows histograms of fluorescence immunocytometry corresponding to the profile of surface markers CD50, CD51, CD54, CD55, CD56, and CD58 obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1F:
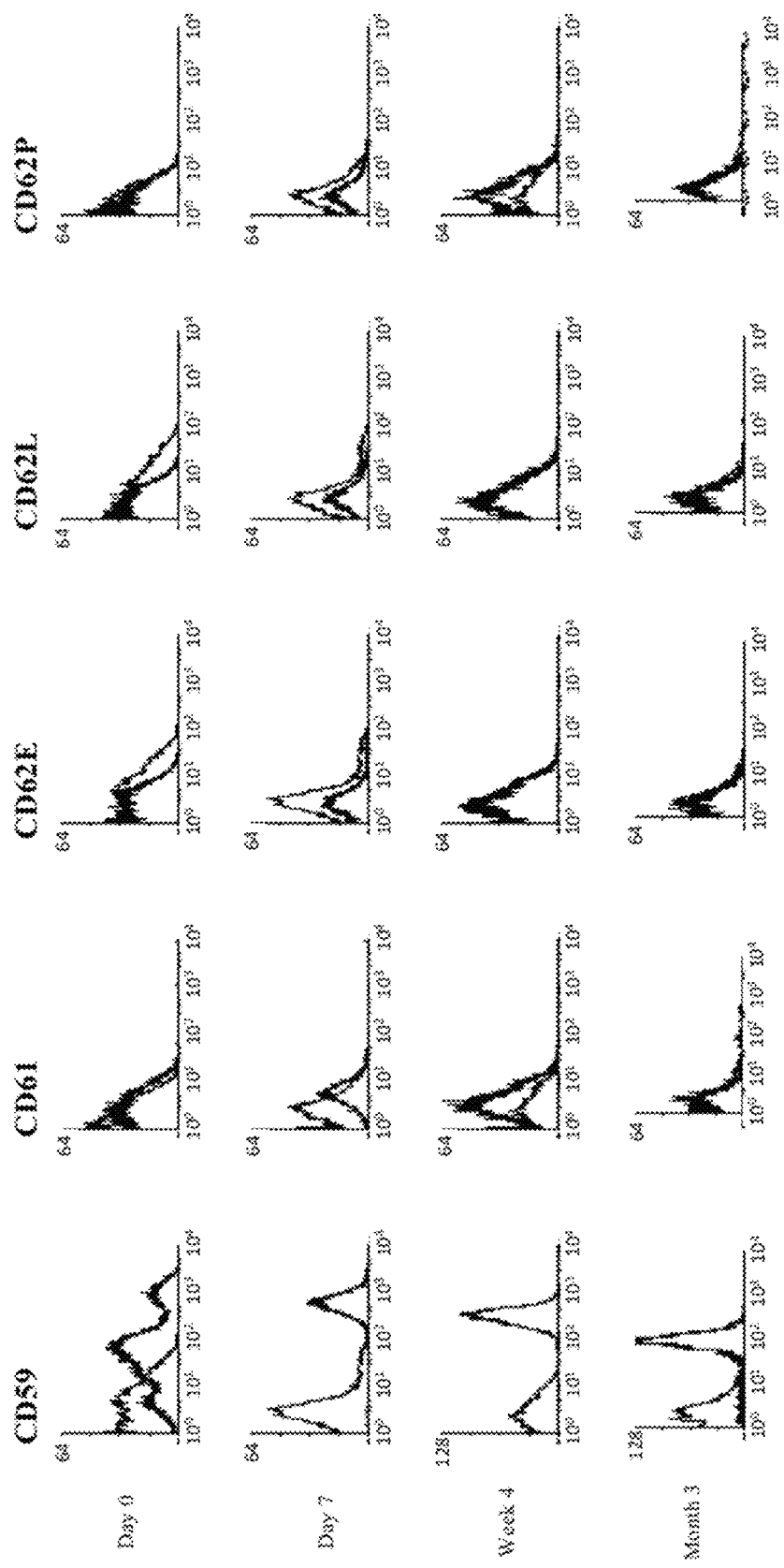
FIG. 1F shows histograms of fluorescence immunocytometry corresponding to the profile of surface markers CD59, CD61, CD62E, CD62L, CD62P obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1G:
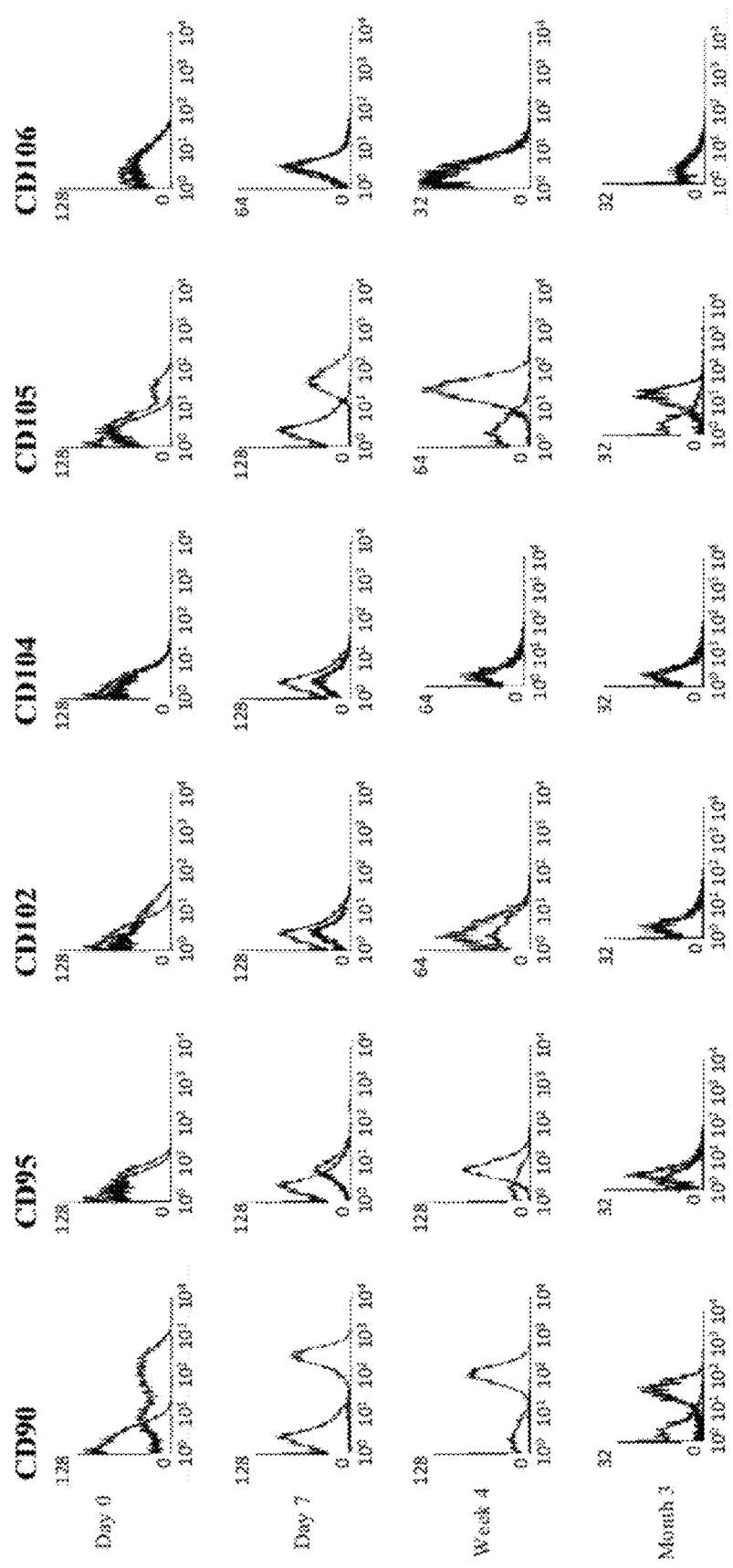
FIG. 1G shows histograms of fluorescence immunocytometry corresponding to the profile of surface markers CD90, CD95, CD102, CD104, CD105, and CD106 obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 1I:
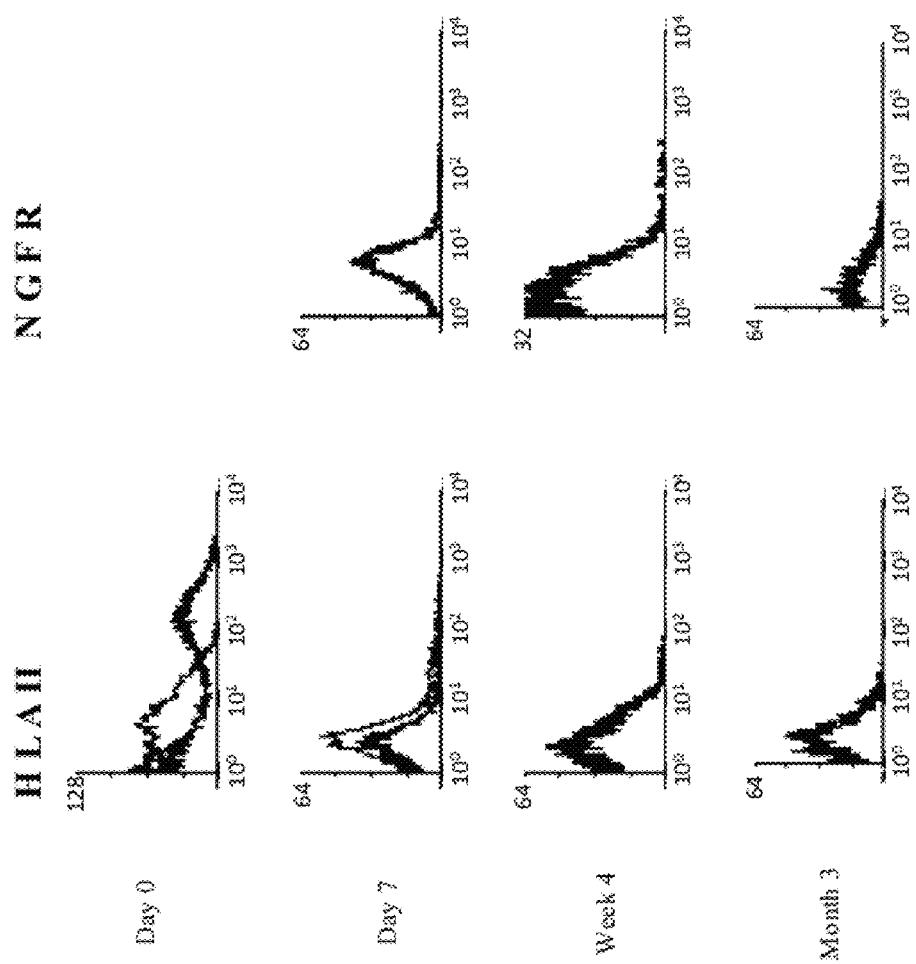
FIG. 1I shows histograms of fluorescence immunocytometry corresponding to the profile of surface markers HLA II and NGFR obtained from cells isolated from liposuction samples of a healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2A:
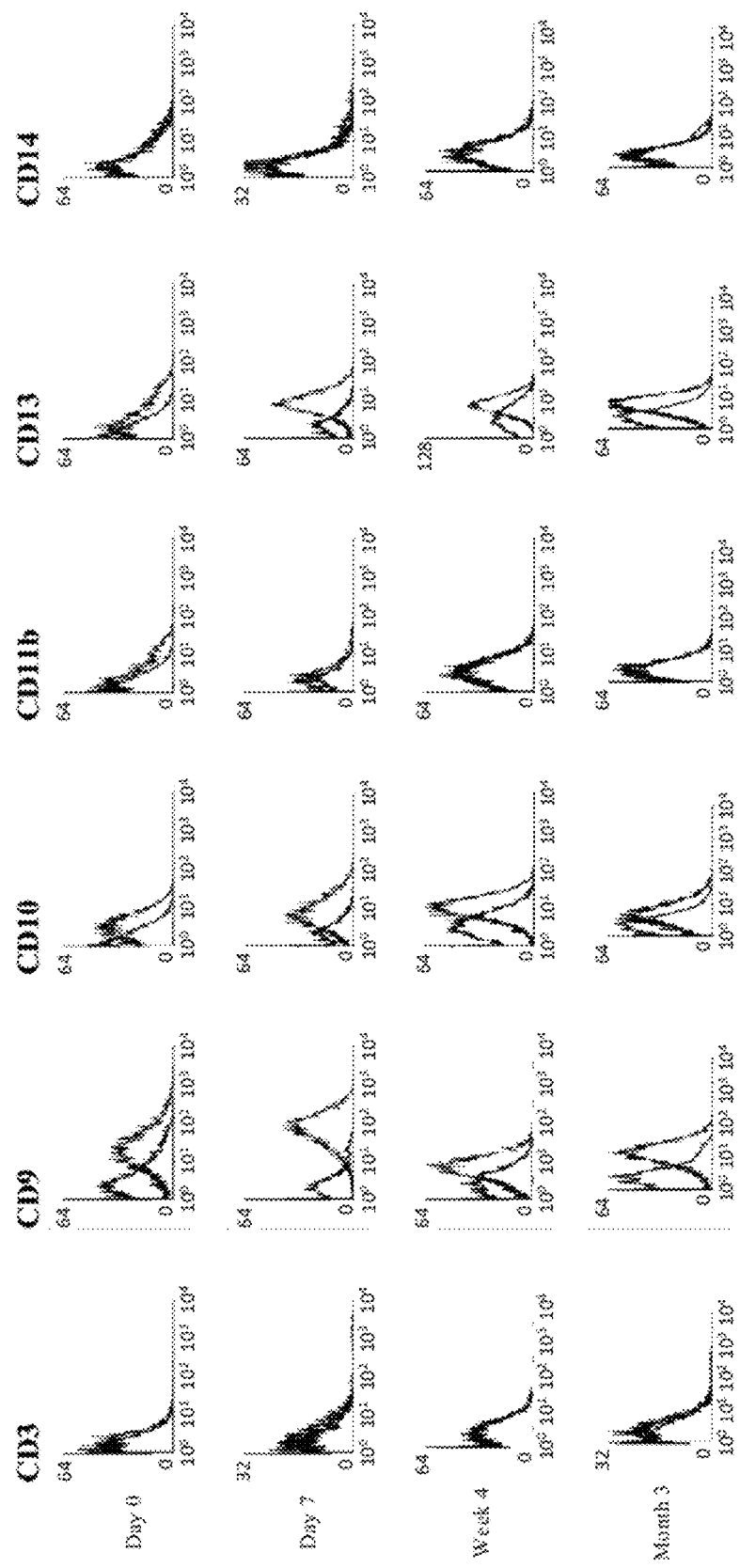
FIG. 2A shows the histograms of fluorescence immunocytometry corresponding to the profile of surface markers CD3, CD9, CD10, CD11b, CD13, and CD14 obtained from cells isolated from liposuction samples from a second healthy donor on Day 0, day 7 of culturing, after 4 weeks of culturing, and after 3 months of culturing. The results show the evolution over time of the markers studied in the cell cultures, indicating in each case the particular time period to which the analyzed cells belong.
Figure 2B:
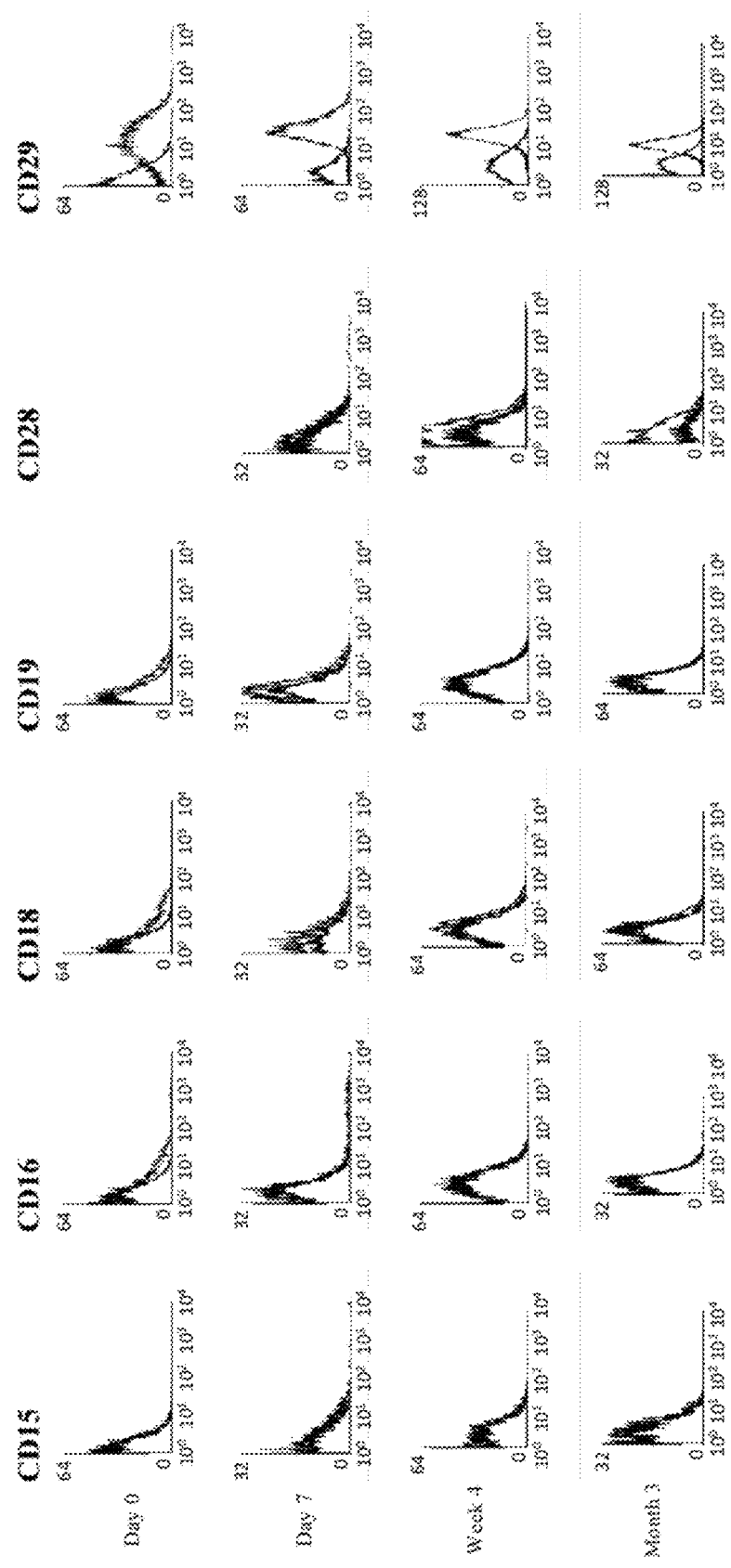
FIG. 2B shows histograms of fluorescence immunocytometry corresponding to the profile of surface markers CD15, CD16, CD18, CD19, CD28, and CD 29 obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2C:
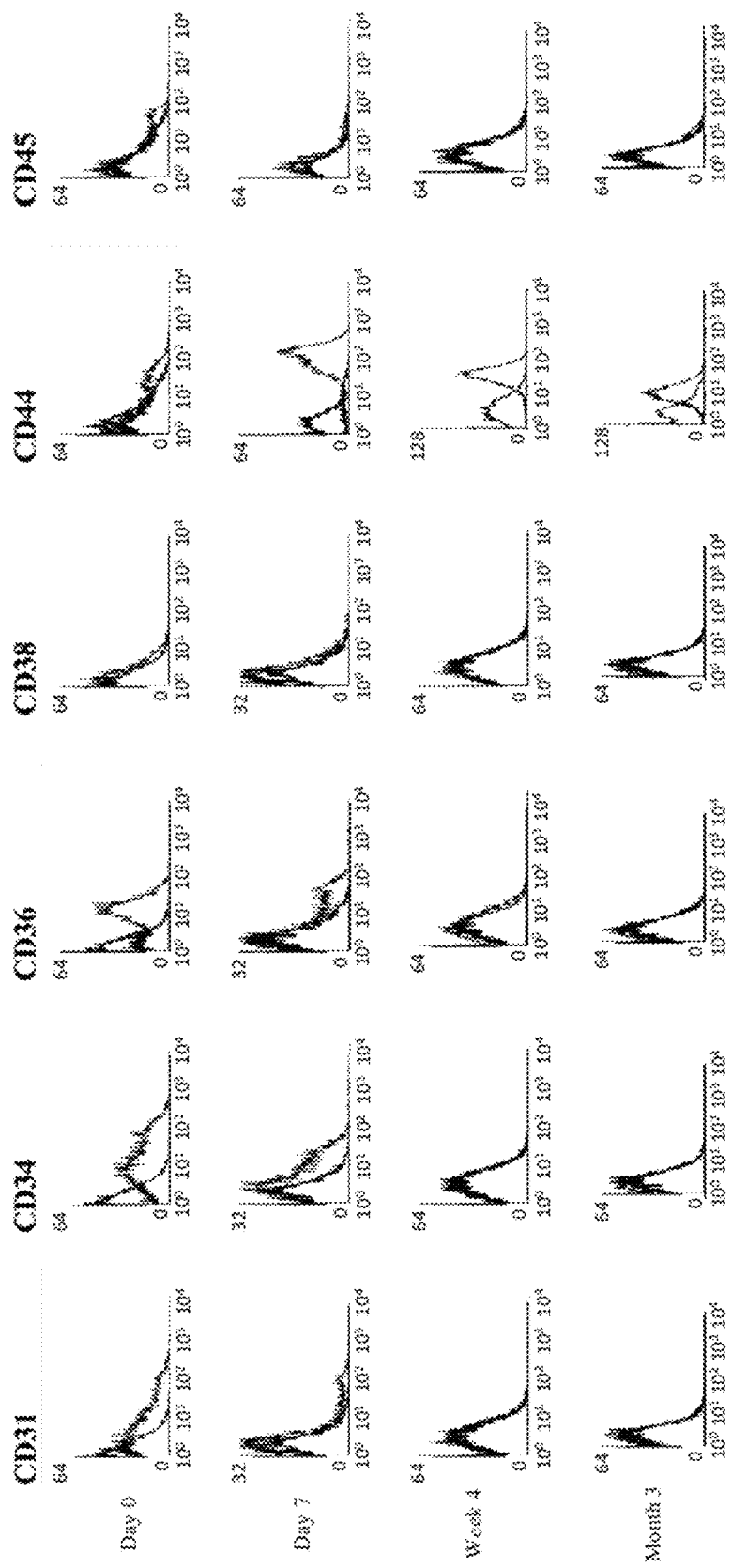
FIG. 2C shows histograms of fluorescence immunocytometry corresponding to the profile of surface markers CD31, CD34, CD36, CD38, CD44, and CD45 obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2D:
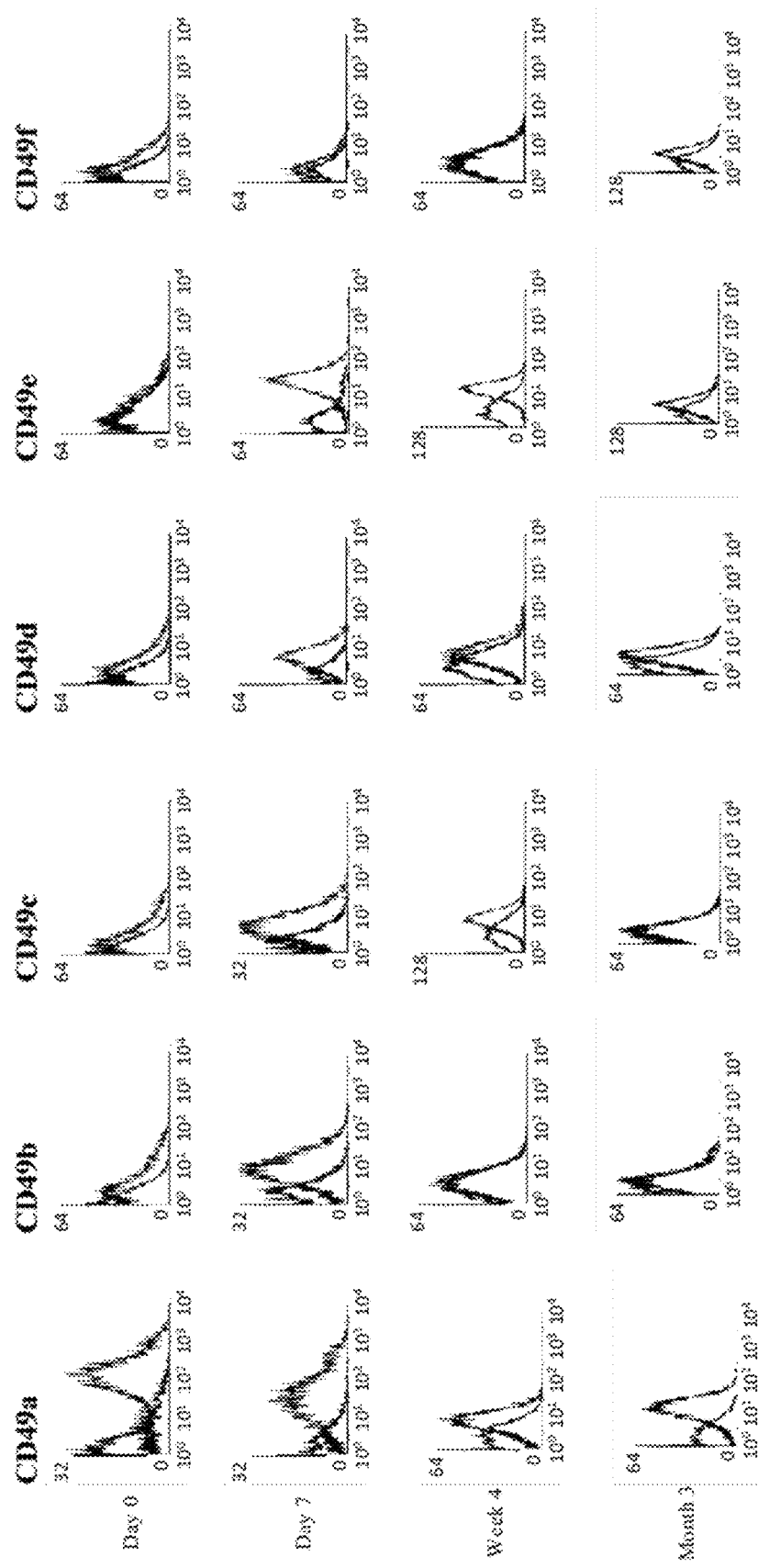
FIG. 2D shows histograms of fluorescence immunocytometry corresponding to the profile of surface markers CD49a, CD49b, CD49c, CD49d, CD49e, and CD49f obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2E:
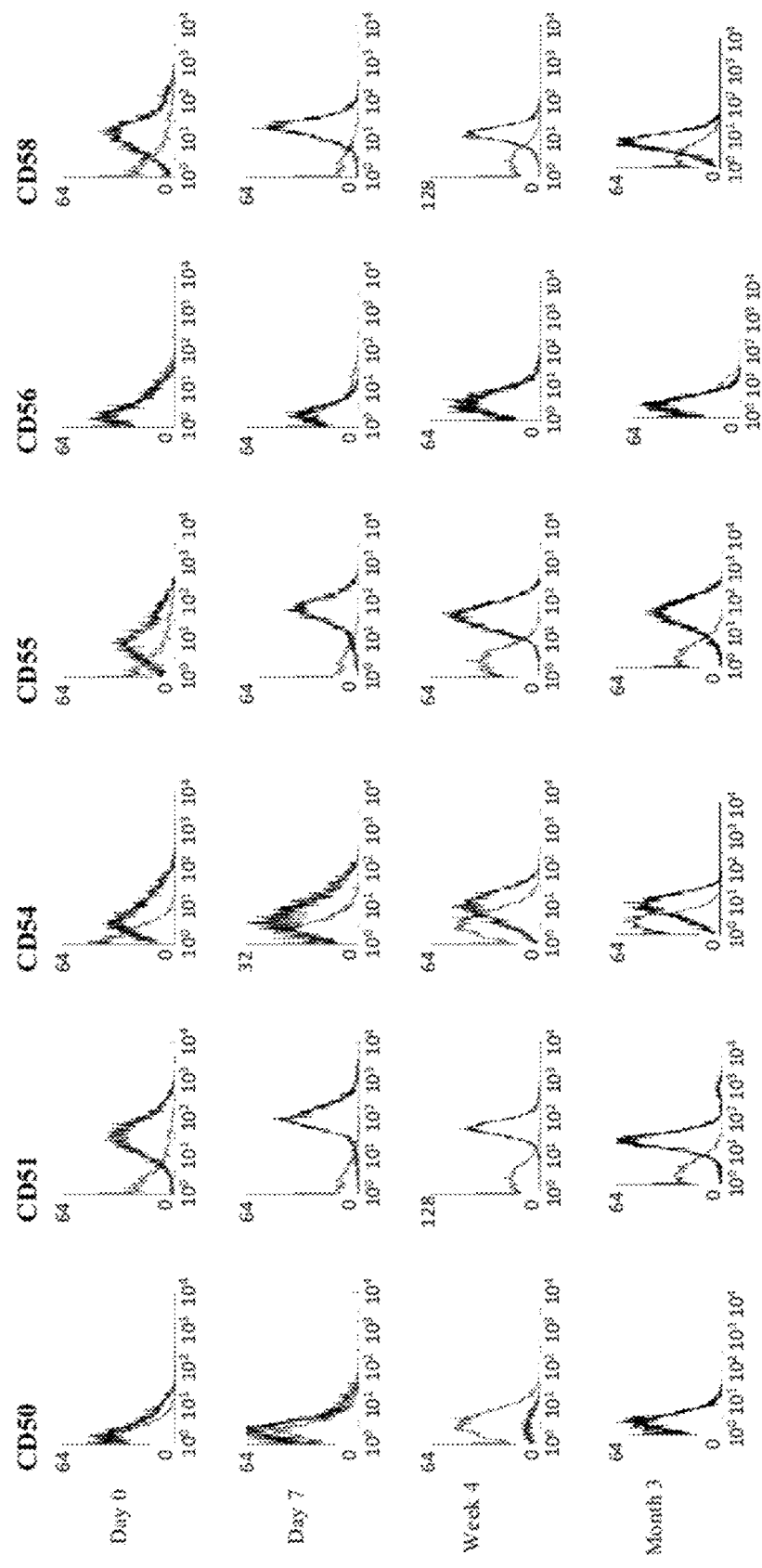
FIG. 2E shows histograms of fluorescence immunocytometry corresponding to the profile of surface markers CD50, CD51, CD54, CD55, CD56, and CD58 obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2G:
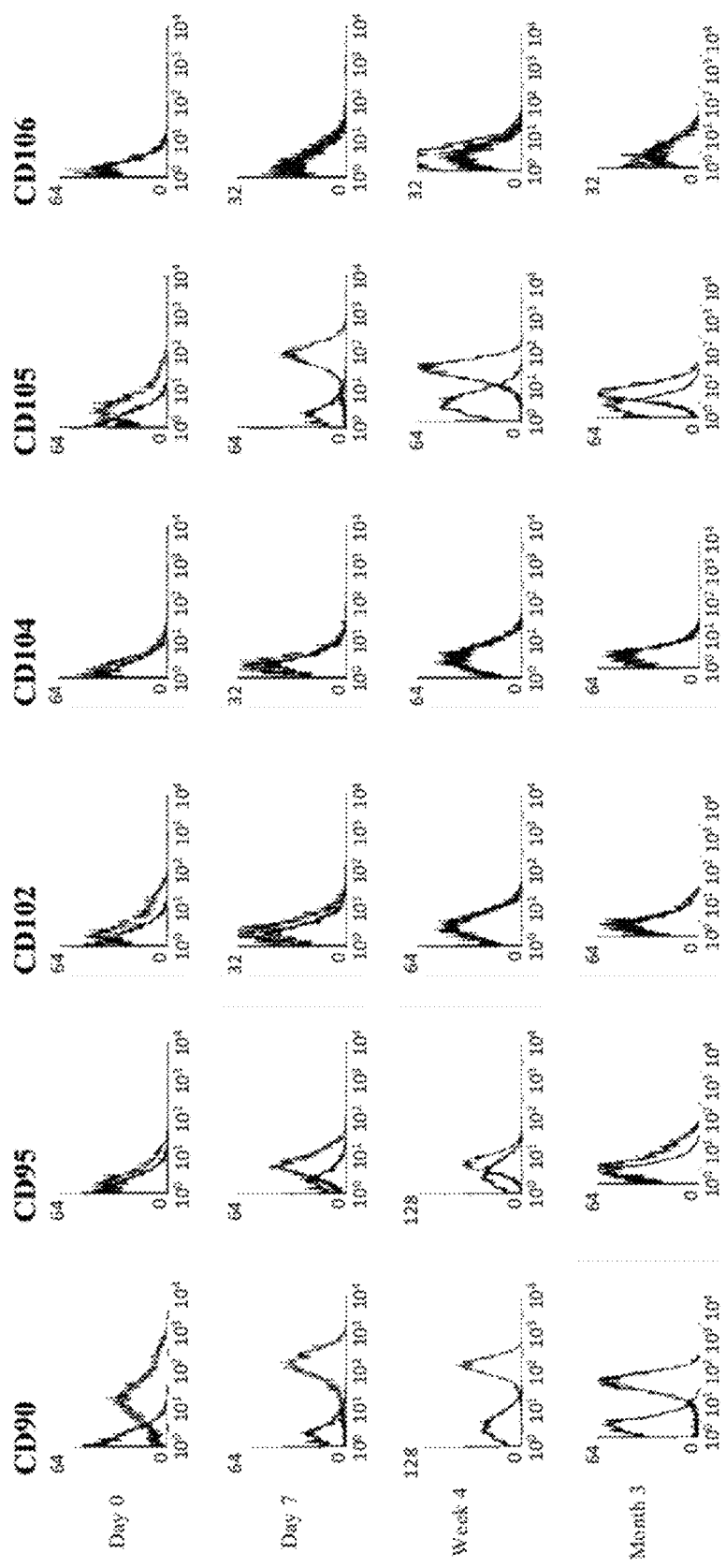
FIG. 2G shows histograms of fluorescence immunocytometry corresponding to the profile of surface markers CD90, CD95, CD102, CD104, CD105, and CD106 obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2H:
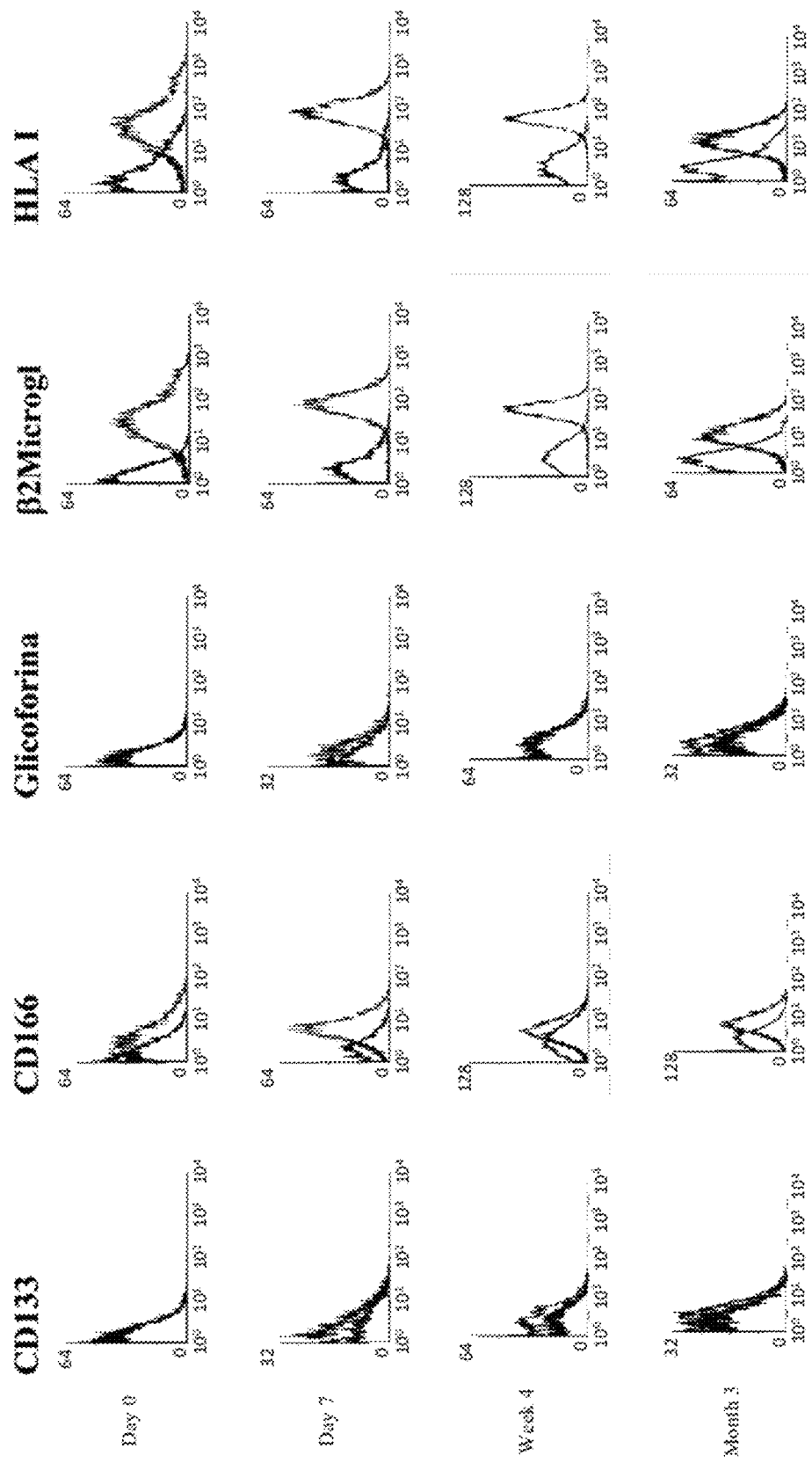
FIG. 2H shows histograms of fluorescence immunocytometry corresponding to the profile of surface markers CD133, CD166, glycophorin, β2Microg1, and HLA I obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 2I:
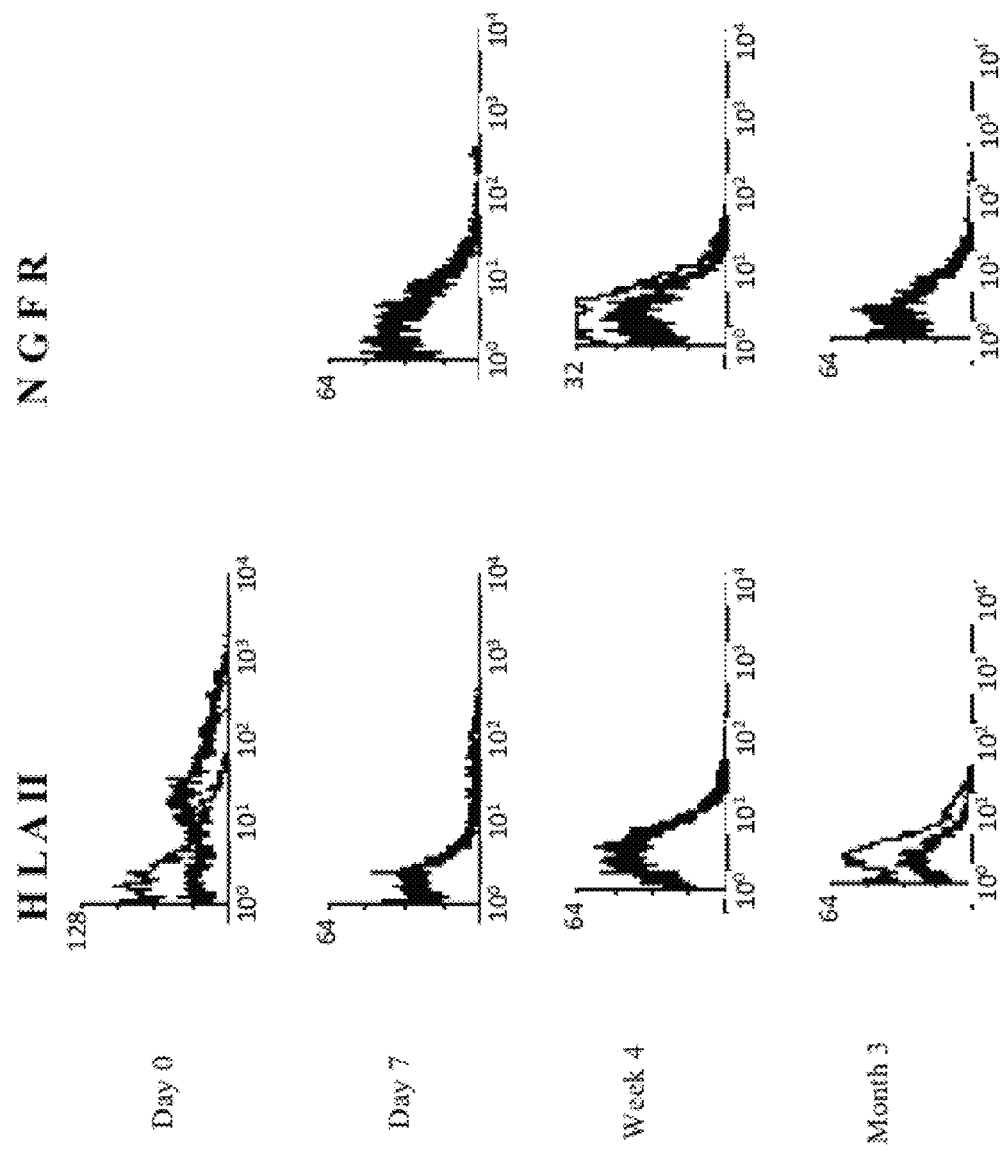
FIG. 2I shows histograms of fluorescence immunocytometry corresponding to the profile of surface markers HLA II and NGFR obtained from cells isolated from liposuction samples from a second healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3A:
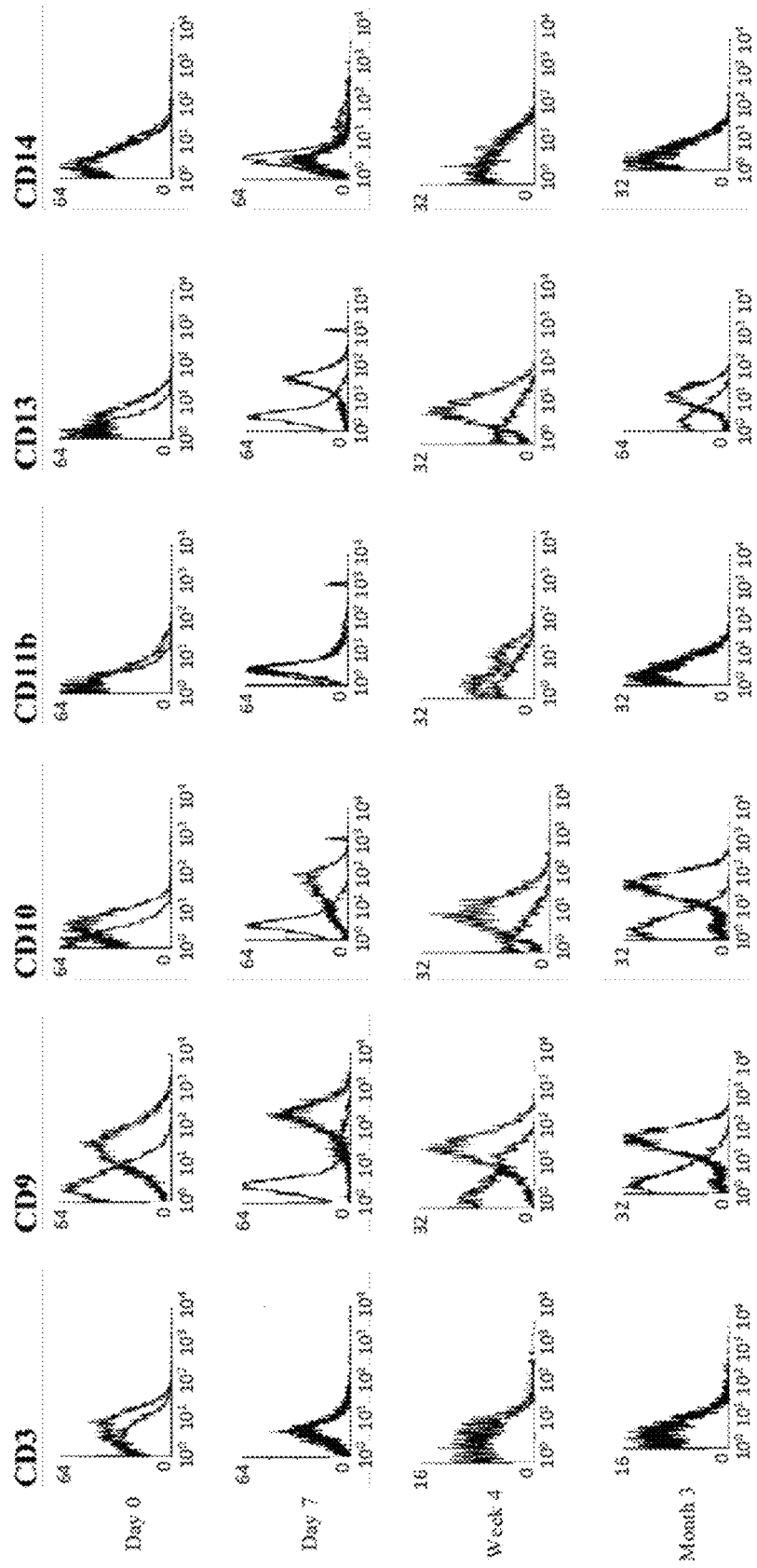
FIG. 3A shows the histograms of fluorescence immunocytometry corresponding to the profile of surface markers CD3, CD9, CD10, CD11b, CD13, and CD14 obtained from cells isolated from liposuction samples from a third healthy donor on Day 0, day 7 of culturing, after 4 weeks of culturing, and after 3 months of culturing. The results show the evolution over time of the markers studied in the cell cultures, indicating in each case the particular time period to which the analyzed cells belong.
Figure 3B:
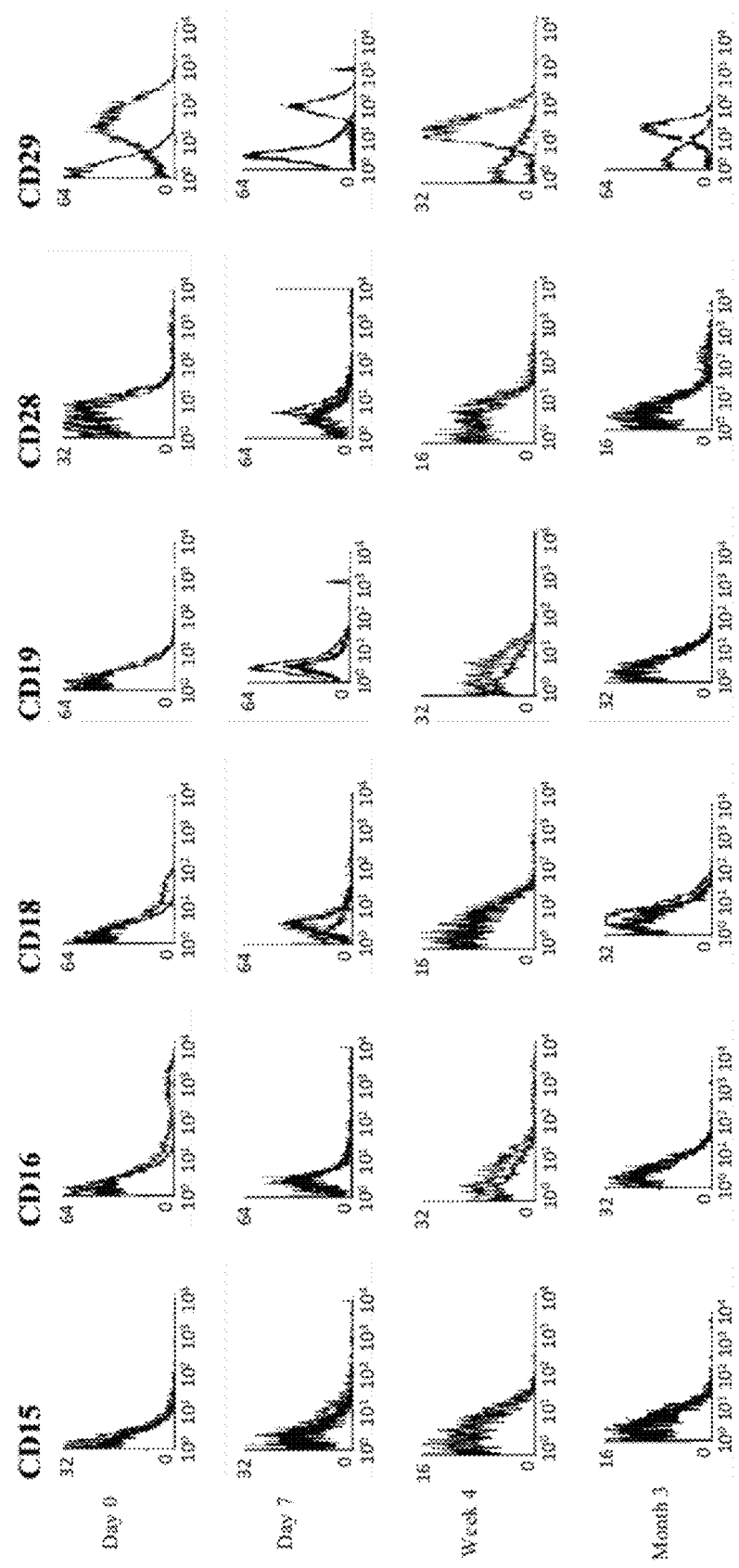
FIG. 3B shows histograms of fluorescence immunocytometry corresponding to the profile of surface markers CD15, CD16, CD18, CD19, CD28, and CD 29 obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3C:
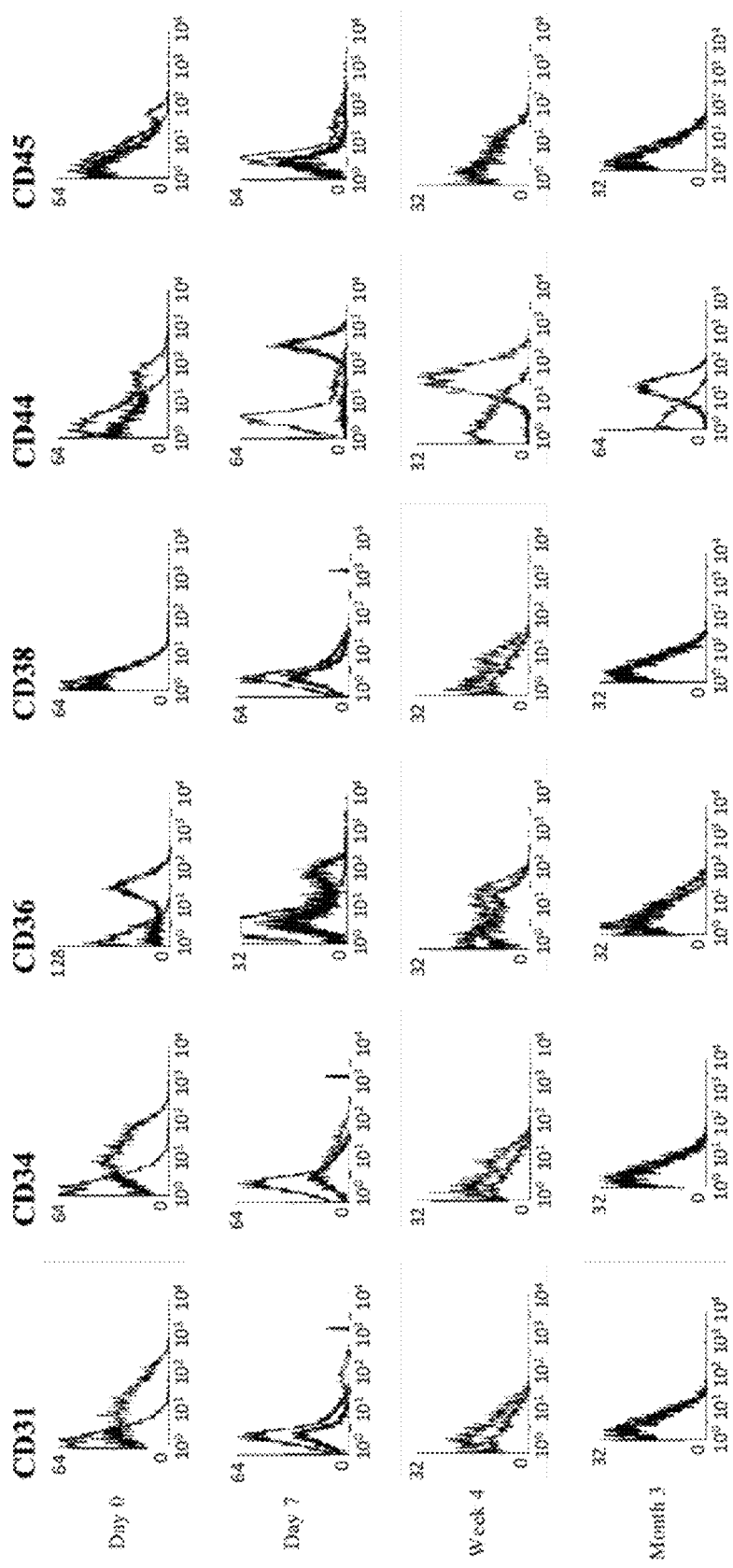
FIG. 3C shows histograms of fluorescence immunocytometry corresponding to the profile of surface markers CD31, CD34, CD36, CD38, CD44, and CD45 obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3D:
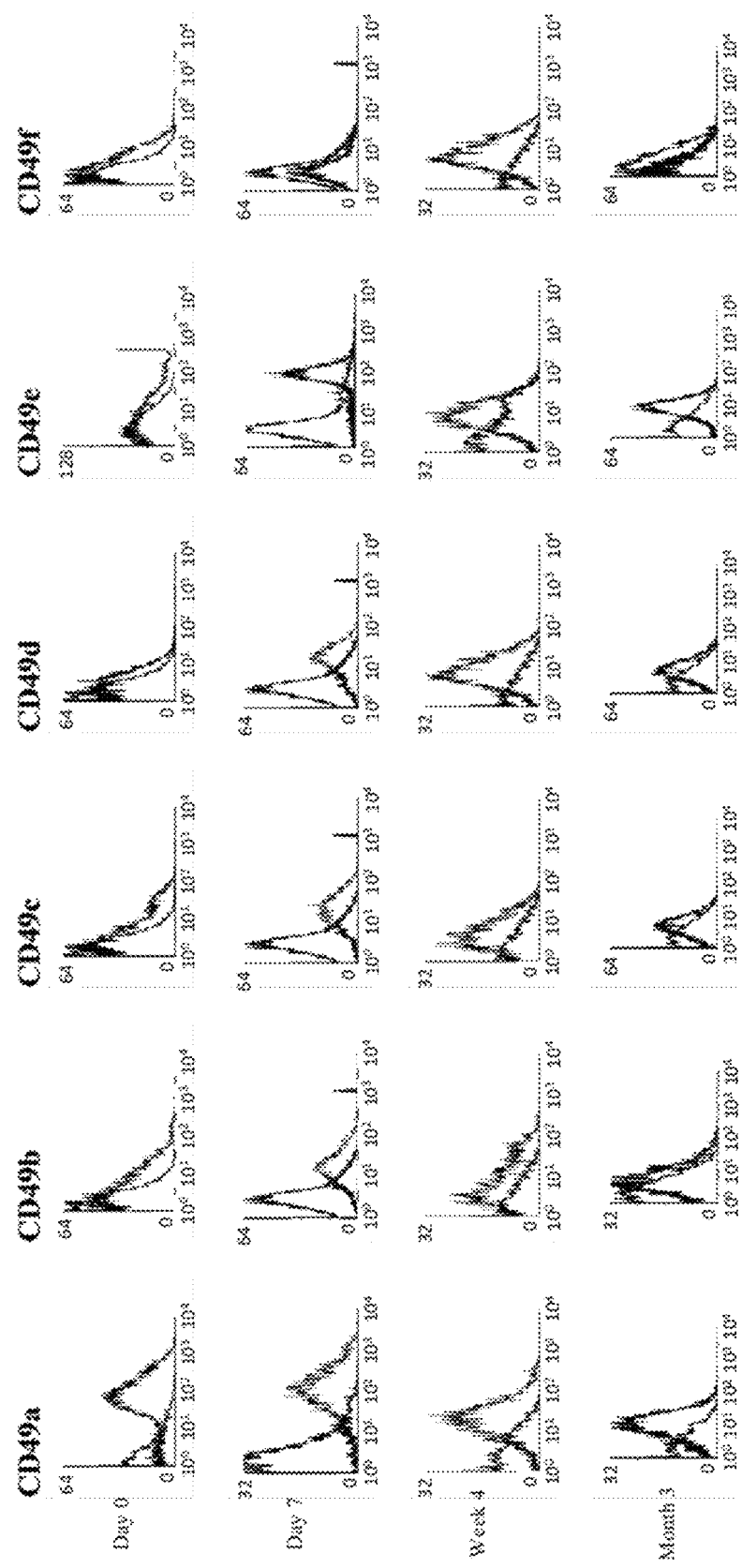
FIG. 3D shows histograms of fluorescence immunocytometry corresponding to the profile of surface markers CD49a, CD49b, CD49c, CD49d, CD49e, and CD49f obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3E:
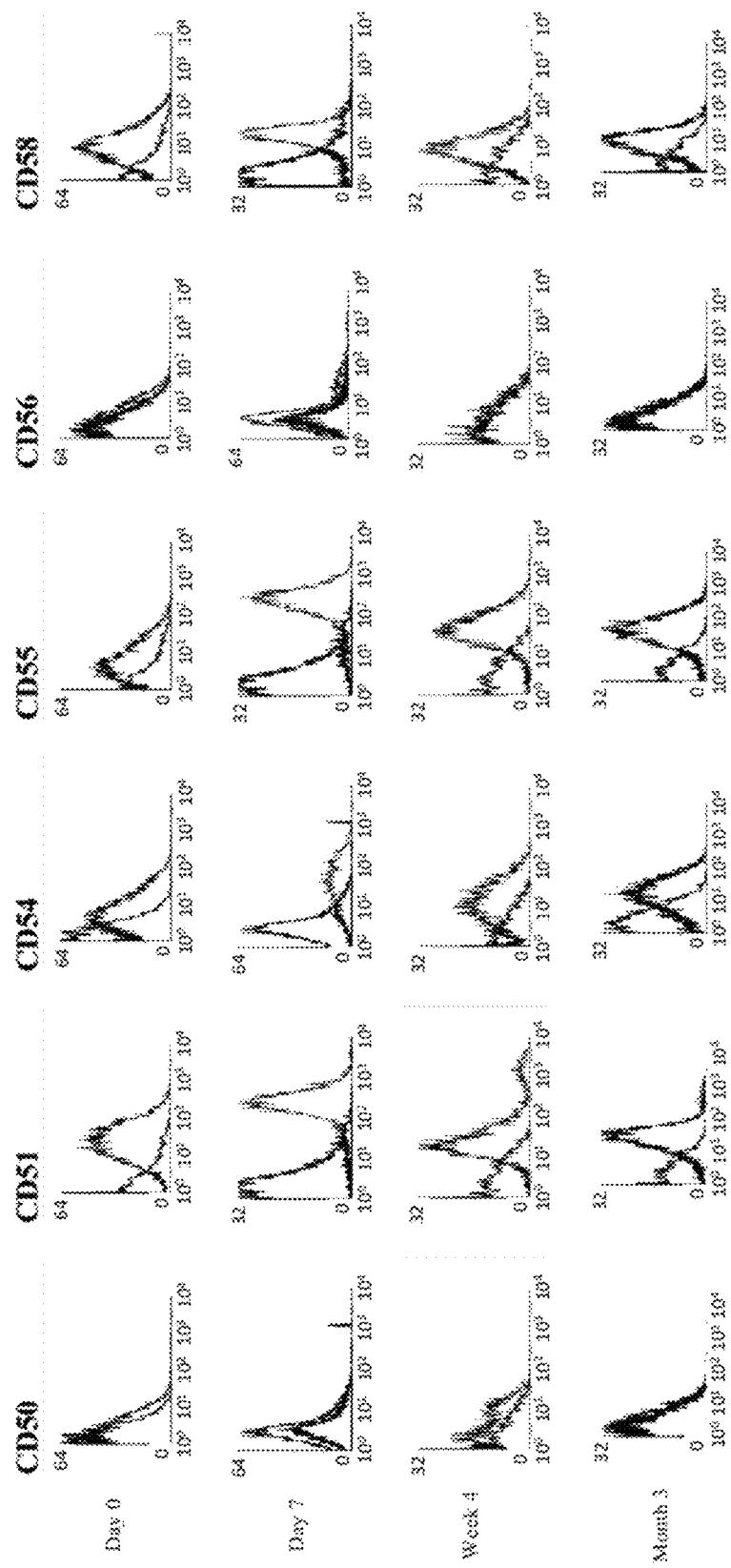
FIG. 3E shows histograms of fluorescence immunocytometry corresponding to the profile of surface markers CD50, CD51, CD54, CD55, CD56, and CD58 obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3F:
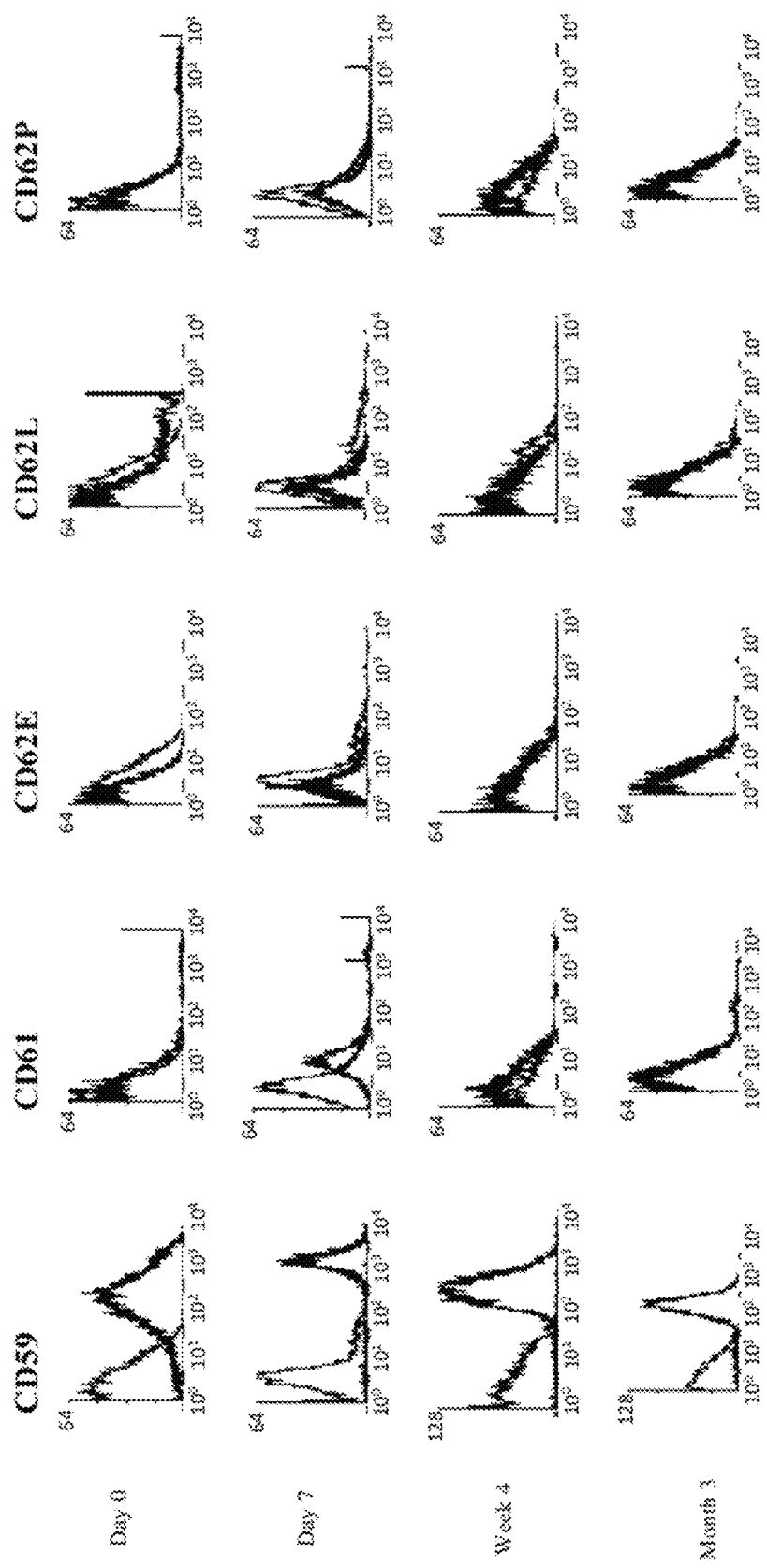
FIG. 3F shows histograms of fluorescence immunocytometry corresponding to the profile of surface markers CD59, CD61, CD62E, CD62L, CD62P obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3G:
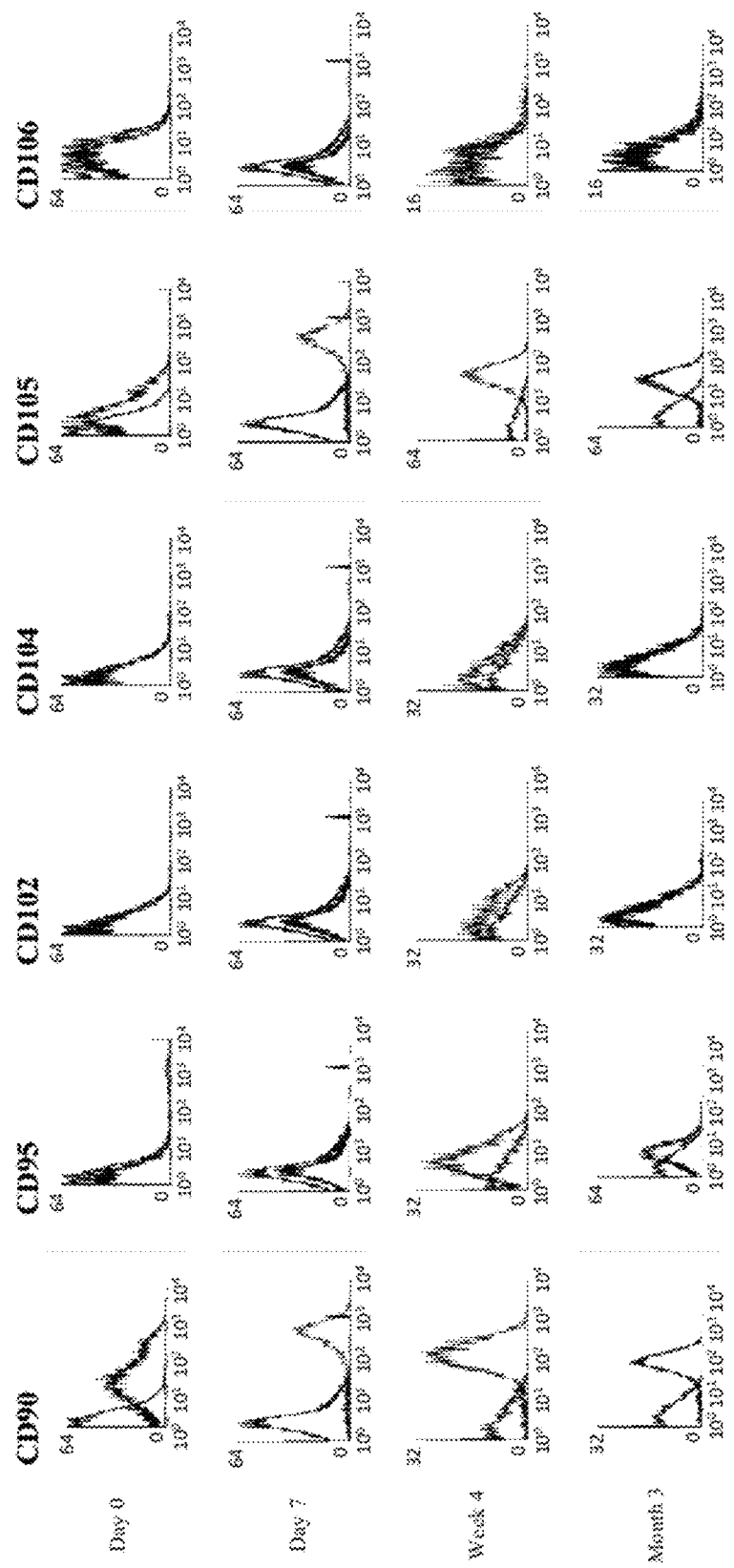
FIG. 3G shows histograms of fluorescence immunocytometry corresponding to the profile of surface markers CD90, CD95, CD102, CD104, CD105, and CD106 obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3H:
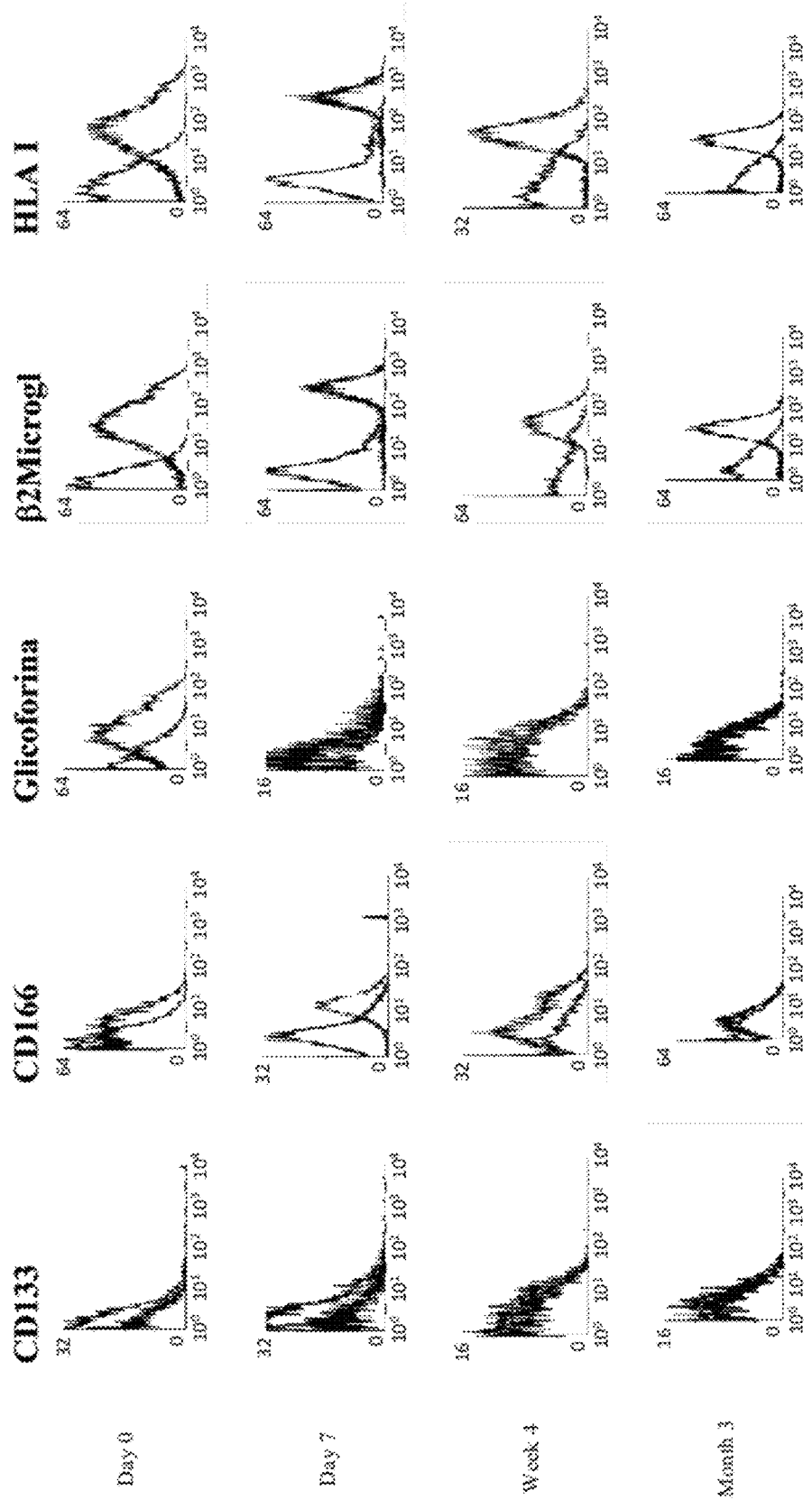
FIG. 3H shows histograms of fluorescence immunocytometry corresponding to the profile of surface markers CD133, CD166, glycophorin, β2Microg1, and HLA I obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.
Figure 3I:
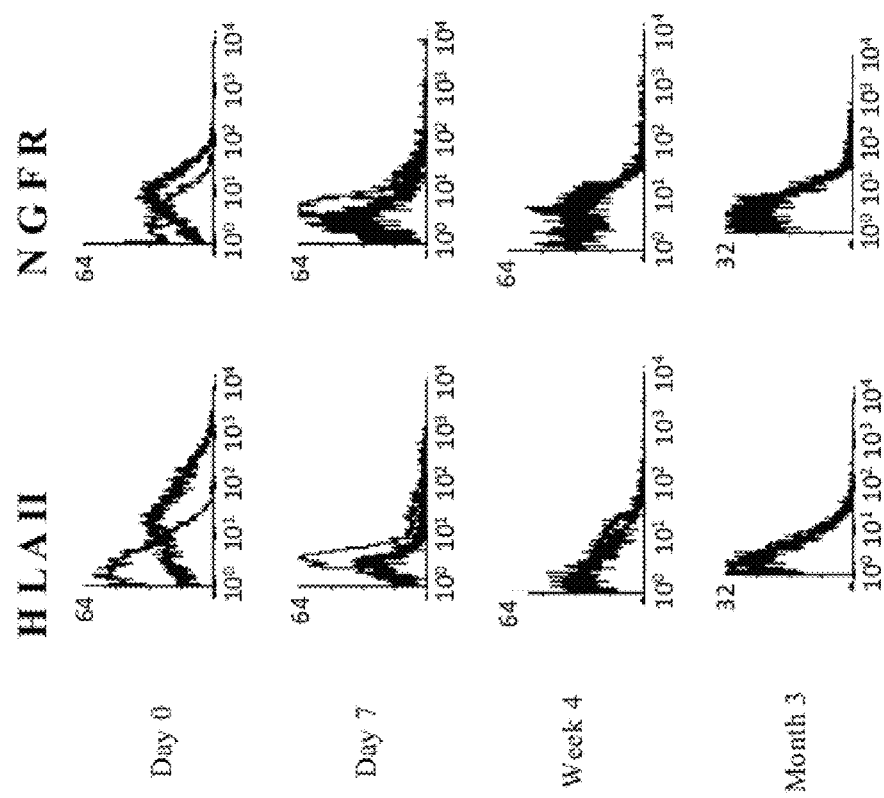
FIG. 3I shows histograms of fluorescence immunocytometry corresponding to the profile of surface markers HLA II and NGFR obtained from cells isolated from liposuction samples from a third healthy donor on day 0, day 7 of culturing, after 4 weeks of culturing, and after 3 months of culturing. The results show the evolution over time of the markers studied in the cell cultures, indicating in each case the particular time period to which the analyzed cells belong.

FIGS. 1A-1I, 2A-2I, and 3A-3I show the histograms grouped by donor for a better visualization of the evolution of the markers studied during the culturing, indicating in each case what time in the culture period the analyzed cells belong.

The analysis of surface markers at different times allowed their presence or absence to be determined, as well as their behaviour during the culture process. The results obtained show that the cell populations isolated from the different healthy donors show a homogeneous behaviour in their phenotype characterization.

From the analysis of the expression profile of surface markers (FIGS. 1A-1I, 2A-2I, and 3A-3I), 3 criteria were used to determine which markers define the cell population and allow it to be identified and differentiated with respect to other types of cell populations. These criteria were:

1. Discard those markers that vary from one sample to the other or over time during culturing.
2. Verify that those that are positive are also positive at time zero (recently isolated cells).
3. Select them as a function of their biological relevance, discarding markers characteristic of specific cell types (for example, CD3 is a marker exclusive to lymphocytes).

Applying these criteria, the multipotent adult cells isolated from non-osteochondral mesenchymal tissue provided by the present invention is characterized by being positive for CD9<+>, CD10<+>, CD13<+>, CD29<+>, CD44<+>, CD49A<+>, CD51<+>, CD54<+>, CD55<+>, CD58<+>, CD59<+>, CD90<+> and CD105<+>, and for lacking expression of CD11b, CD14, CD15, CD16, CD31, CD34, CD45, CD49f, CD102, CD104, CD106 and CD133.

Example 2

In Vitro Differentiation of Multipotent Adult Cells from Human Non-Osteochondral Mesenchymal Tissue into Bone Phenotype Cells In the differentiation assay, characterized human multipotent adult cells of the present invention were used. The cells were isolated from the 3 samples of analyzed lipoaspirates, each corresponding to a healthy donor (Example 1). The multipotent adult cells were isolated and characterized as mentioned in Example 1. A sample of mesenchymal stem cells (MSC) of human bone marrow was used as positive control.

The isolated cells were seeded at a density of 10,000 cells/$cm^2$ onto 6-well plates (one plate per sample), and were incubated in standard culture medium (DMEM, 10% FBS, L-Glutamine 2 mM and antibiotic). After two days of culturing, the culture medium of one of the wells (control) is replaced with fresh medium, and the remaining wells with osteogenesis inducing medium, which contains the standard culture medium with the following added:

Dexamethasone 100 M
Ascorbic acid 50 µM
p-Glycerophosphate 10 mM

The cells were cultured for 3 weeks in normal conditions, changing the medium every 2-3 days. After three weeks, the presence of mineralized deposits of calcium phosphate can be seen, which indicates the presence of osseus nodules. These nodules are detected by staining with Alizarin red (Standford et al., 1995). Specifically, the medium was eliminated, the cells were washed twice with PBS and fixed with 70% cold ethanol for 30 minutes at room temperature. The fixed wells were then washed with PBS and stained with Alizarin red (40 mM, pH 4.1) for 10 minutes at room temperature. The stained cells were washed with abundant water, and the precipitates of calcium phosphate, which appear strongly stained red, were examined under the microscope.

Figure 4B:
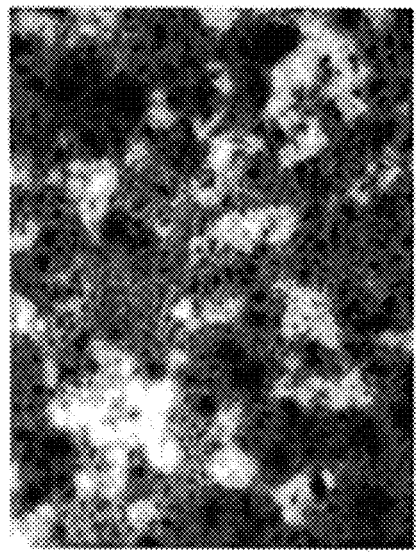
FIG. 4b shows the cells of the invention, multipotent adult cells from non-osteochondral mesenchymal tissue, incubated in osteogenic medium for the first week.
Figure 4D:
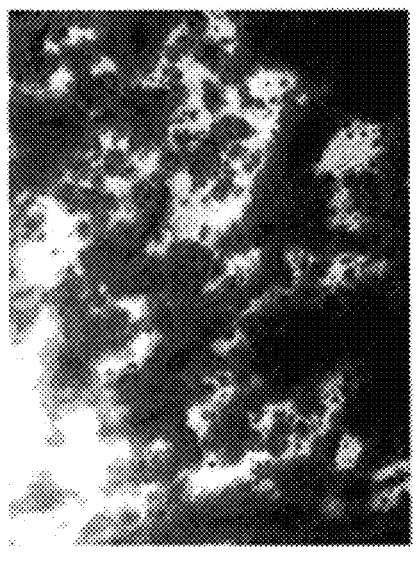
FIG. 4d shows the multipotent adult cells of the invention, incubated in osteogenic medium during the third week.
Figure 4A:
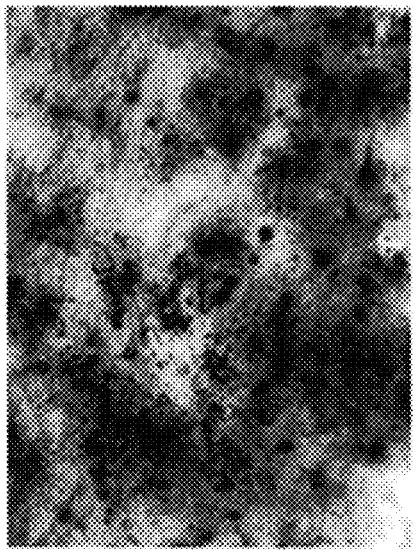
FIG. 4a shows microphotographs of mesenchymal stem cells from human bone marrow (positive control) incubated in osteogenic medium for 3 weeks.
Figure 4C:
FIG. 4c shows the multipotent adult cells of the invention, incubated in osteogenic medium for the second week.

FIGS. 4a-4d show microphotographs of the osteo-induced cells stained with Alizarin red. Although the formation of calcium phosphate is quicker in the sample corresponding to MSC from bone marrow which acts as a positive control (FIG. 4a), in the 3 samples from the adipose tissue, the formation of large quantities of bone matrix can be discerned, although with differing intensity in each of the samples. All wells in which osteogenesis was induced showed the same behaviour and in the control wells (not submitted to osteogenic stimuli) the formation of bone matrix was not detected. No relationship was seen between the amount of bone matrix formed and the time that each sample was being cultured after isolation from the tissue (between 3 and 9 weeks).

Example 3

In Vitro Differentiation of Multipotent Adult Cells from Human Non-Osteochondral Mesenchymal Tissue into Muscle Phenotype Cells In the differentiation assay, characterized human multipotent adult cells of the present invention were used. The cells were isolated from the 3 samples of analyzed lipoaspirates, each corresponding to a healthy donor (Example 1). The multipotent adult cells were isolated and characterized as mentioned in Example 1. A sample of MSC of human bone marrow was used as positive control.

The isolated cells were seeded at a density of 10,000 cells/cm$^2$ into standard culture medium (DMEM, 10% FBS, L-Glutamine 2 mM and antibiotic). After two days of culturing, the culture medium of one of the wells (control) was replaced with fresh medium, and the remaining wells with myogenesis inducing medium (Wakitani et al., 1995), which contains the standard culture medium with the following added:

Ascorbate-2-phosphate 0.1 mM
Dexamethasone 0.01 μM
ITS+1 (Sigma-Aldrich)
5-Azacytidine 3 μM After 24 hours, the medium was replaced by standard culture medium, and the cells were cultured for 2-3 weeks, changing the medium every 2-3 days. After this time, the cells acquired an elongated phenotype, formed fibrillar structures and some cell fusions can be seen. To detect the myoblast phenotype, the cells obtained were fixed with paraformaldehyde (PFA) at 4% and incubated with an antibody against the heavy chain of myosin, which is the specific antigen for muscle. The results confirm the differentiation of the human multipotent adult cells of the invention into muscle phenotype cells.

Example 4

In Vitro Differentiation of Multipotent Adult Cells from Human Non-Osteochondral Mesenchymal Tissue into Neuronal Phenotype Cells In the differentiation assay, characterized human multipotent adult cells of the present invention were used. The cells were isolated from the 3 samples of analyzed lipoaspirates, each corresponding to a healthy donor (Example 1). The multipotent adult cells were isolated and characterized as mentioned in Example 1. A sample of MSC from human bone marrow was used as positive control.

The isolated cells were seeded at low density, $3\times10^3$ cells/cm$^2$, into standard culture medium (DMEM, 10% FBS, L-Glutamine 2 mM and antibiotic), supplemented with 10 ng/ml bFGF and incubated for 24-36 hours to yield a large number of cells. The wells were then washed and neuron-inducing medium was added (Black and Woodbury, 2001), comprising:

αMEM
BHA 200 μM
Penicillin/streptomycin
L-Glutamine 2 mM
Forskolin 10 μM
2% DMSO
Hydrocortisone 1 μM
Insulin 5 μg/ml
ClK 25 mM
Valproic acid 2 mM A few hours after induction, a morphological change could be observed; the cells acquired a rounded shape and very refringent, with prolongations with a similar appearance to axons and dendrites of nerve cells. After 3 days, the cells obtained were fixed with PFA at 4% and incubated with antibodies against neuron specific antigens NF-200 and TuJ1. The results confirm the differentiation of the human multipotent adult cells of the invention into muscle phenotype cells.

REFERENCES

Osawa M., Hanada K., Hanada H. and Nakauchi H. (1996) Science 273, 242-245.
Morrison S. J., Uchida N. and Weissman I. L. (1995) Annu. Rev. Cell Dev. Biol. 11, 35-71.
Ivanova N. B., Dimos J. T., Schaniel C., Hackney J. A., Moore K. A., Lemischka I. R. (2002) Science 298, 601-604.
Phillips R L. (2000) Curr Top Microbiol Immunol. 251, 13-19.
Ramalho-Santos M, Yoon S, Matsuzaki Y, Mulligan R C, Melton D A. (2002) Science 298, 597-600.
Friedenstein A J, Gorskaja J F, Kulagina N N, Exp Hematol. 1976 September; 4(5):267-74.
Caplan A l J Orthop Res. 1991 September; 9(5): 641-50
Pittenger, M. F. et al. (1999) Science 284: 143-147
Beresford J N, Bennett J H, Devlin C, Leboy P S, Owen M E, J Cell Sci. 1992 June; 102(Pt 2): 341-51
Yoo J U, Johnstone B, Clin Orthop. 1998 October; (355 Suppl): 573-81
Wakitani S. et al. (1995) Muscle Nerve 18: 1417-1426.
Haynesworth S E, Goshima J, Goldberg V M, Caplan A l, Bone. 1992; 13(1): 81-8.
Sanchez-Ramos J, Song S, Cardozo-Pelaez F, Hazzi C, Stedeford T, Willing A, Freeman T B, Saporta S, Janssen W, Patel N, Cooper D R, Sanberg P R, Exp Neurol. 2000 August; 164(2): 247-56.
Rogers J J, Young H E, Adkison L R, Lucas P A, Black A C Jr, Am Surg. 1995 March; 61(3): 231-6.
Zuk, P. A. et al. (2001) Tissue Eng 7: 211-228.
Jiang Y, Vaessen B, Lenvik T, Blackstad M, Reyes M, Verfaillie C M, Exp Hematol. 2002 August; 30(8):896-904.
Caplan A l, Bruder S P, Trends Mol Med. 2001 June; 7(6): 259-64. 5
Stanford. C. M. et al. (1995) J Biol Chem 270: 9420-9428.

Young H E, Ceballos E M, Smith J C, Mancini M L, Wright R P, Ragan B L, Bushell I, Lucas P A. In vitro Cell Dev Biol Anim. 1993 September; 29 A(9): 723-36.

The invention claimed is:

1. A method for identifying a substantially homogeneous, consecutively passaged cell population comprising multipotent adult cells, which (a) is isolated from human non-osteochondral mesenchymal tissue, (b) expresses CD9, CD10, CD13, CD29, CD44, CD49a, CD51, CD54, CD55, CD58, CD59, CD90 and CD105; and (c) lacks expression of CD11b, CD14, CD15, CD16, CD31, CD34, CD45, CD49f, CD102, CD104, CD106 and CD133, the method comprising:

(a) incubating the cell population with labelled antibodies that bind specifically to CD9, CD10, CD13, CD29, CD44, CD49a, CD51, CD54, CD55, CD58, CD59, CD90, CD105, CD11b, CD14, CD15, CD16, CD31, CD34, CD45, CD49f, CD102, CD104, CD106, and CD133; and (b) identifying a substantially homogenous cell population by detecting the presence of binding of all of the labeled antibodies that bind specifically to CD9, CD10, CD13, CD29, CD44, CD49a, CD51, CD54, CD55, CD58, CD59, CD90 and CD105, and absence of binding of all of the labeled antibodies that bind specifically to CD11 b, CD14, CD15, CD16, CD31, CD34, CD45, CD49f, CD102, CD104, CD106 and CD133 on the multipotent adult cells.

2. A method for isolating a substantially homogeneous, consecutively passaged cell population comprising multipotent adult cells, which (a) is isolated from human non-osteochondral mesenchymal tissue, (b) expresses CD9, CD10, CD13, CD29, CD44, CD49a, CD51, CD54, CD55, CD58, CD59, CD90 and CD105; and (c) lacks expression of CD11b, CD14, CD15, CD16, CD31, CD34, CD45, CD49f, CD102, CD104, CD106 and CD133, wherein the method comprises:

(a) collecting a human non-osteochondral mesenchymal tissue;

(b) obtaining a first cell suspension from the tissue by enzymatic digestion;

(c) sedimenting and resuspending the cells in a culture medium;

(d) culturing the cells on a solid surface, and eliminating cells that show no adhesion to said solid surface;

(e) expanding by consecutively passaging the cells to generate a consecutively passaged cell population;

(f) incubating a second cell suspension isolated from the consecutively passaged cell population with a labelled anti-CD9 antibody, a labelled anti-CD10 antibody, a labelled anti-CD13 antibody, a labelled anti-CD29 antibody, a labelled anti-CD44 antibody, a labelled anti-CD49a antibody, a labelled anti-CD51 antibody, a labelled anti-CD54 antibody, a labelled anti-CD55 antibody, a labelled anti-CD58 antibody, a labelled anti-CD59 antibody, a labelled anti-CD90 antibody, and a labelled anti-CD105 antibody for a positive selection, and a labelled anti-CD11 b antibody, a labelled anti-CD14 antibody, a labelled anti-CD15 antibody, a labelled anti-CD16 antibody, a labelled anti-CD31 antibody, a labelled anti-CD34 antibody, a labelled anti-CD45 antibody, a labelled anti-CD49f antibody, a labelled anti-CD102 antibody, a labelled anti-CD104 antibody, a labelled anti-CD106 antibody, and a labelled anti-CD133 antibody for a negative selection; and (g) selecting the substantially homogeneous, consecutively passaged cell population comprising multipotent adult cells that express CD9, CD10, CD13, CD29, CD44, CD49a, CD51, CD54, CD55, CD58, CD59, CD90 and CD105; and lack expression of CD11b, CD14, CD15, CD16, CD31, CD34, CD45, CD49f, CD102, CD104, CD106 and CD133.

3. The method according to claim 1, wherein the positive and negative cell surface marker profile of the cells of the substantially homogeneous, consecutively passaged cell population is stable over time.

4. The method according to claim 2, wherein the positive and negative cell surface marker profile of the cells of the substantially homogeneous, consecutively passaged cell population is stable over time.

* * * * *